United States Patent
Tomida et al.

(10) Patent No.: US 11,800,989 B2
(45) Date of Patent: Oct. 31, 2023

(54) ELECTRONIC DEVICE, CONTROL METHOD FOR THE ELECTRONIC DEVICE, AND STORAGE MEDIUM

(71) Applicant: CASIO COMPUTER CO., LTD., Tokyo (JP)

(72) Inventors: Takahiro Tomida, Tokyo (JP); Toshihiko Otsuka, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 334 days.

(21) Appl. No.: 17/172,241

(22) Filed: Feb. 10, 2021

(65) Prior Publication Data
US 2021/0267473 A1   Sep. 2, 2021

(30) Foreign Application Priority Data
Feb. 27, 2020   (JP) .................. 2020-031638

(51) Int. Cl.
*A61B 5/00* (2006.01)
*A61B 5/024* (2006.01)
(Continued)

(52) U.S. Cl.
CPC ........ *A61B 5/02427* (2013.01); *A61B 5/0261* (2013.01); *A61B 5/7246* (2013.01);
(Continued)

(58) Field of Classification Search
CPC . A61B 5/02427; A61B 5/0261; A61B 5/7246; A61B 5/7278; A61B 5/742;
(Continued)

(56) References Cited

U.S. PATENT DOCUMENTS

| 7,566,307 B2 | 7/2009 | Inukai et al. |
| 9,107,634 B2 | 8/2015 | Inoue |

(Continued)

FOREIGN PATENT DOCUMENTS

| JP | S6354135 A | 3/1988 |
| JP | 2007082682 A | 4/2007 |

(Continued)

OTHER PUBLICATIONS

Ferrara et al. ("Color flow mapping". 1996) (Year: 1996).*

(Continued)

*Primary Examiner* — Joseph M Santos Rodriguez
(74) *Attorney, Agent, or Firm* — Holtz, Holtz & Volek PC

(57) ABSTRACT

An electronic device acquires pulse wave information indicating a pulse wave of a first portion of a body and pulse wave information indicating a pulse wave of a second portion of the body, based on video information of the body in each of a first video and a second video obtained by imaging the body. The device further acquires, based on a relationship between the pulse wave information of the first portion and the pulse wave information of the second portion acquired from the first video, and a relationship between the pulse wave information of the first portion and the pulse wave information of the second portion acquired from the second video, a measurement result indicating a degree of change in blood flow from when imaging the first video to when imaging the second video.

7 Claims, 16 Drawing Sheets

(51) Int. Cl.
*G06T 7/11* (2017.01)
*G06T 11/00* (2006.01)
*G06T 7/90* (2017.01)
*A61B 5/026* (2006.01)

(52) U.S. Cl.
CPC ............ *A61B 5/7278* (2013.01); *A61B 5/742* (2013.01); *G06T 7/11* (2017.01); *G06T 7/90* (2017.01); *G06T 11/001* (2013.01); *A61B 5/0077* (2013.01); *A61B 2576/00* (2013.01); *G06T 2207/10016* (2013.01); *G06T 2207/30104* (2013.01); *G06T 2210/41* (2013.01)

(58) Field of Classification Search
CPC . A61B 5/0077; A61B 2576/00; A61B 5/4848; A61B 5/6898; A61B 2576/02; A61B 5/02; A61B 5/0033; A61B 5/72; G06T 7/11; G06T 7/90; G06T 11/001; G06T 2207/10016; G06T 2207/30104; G06T 2210/41
See application file for complete search history.

(56) References Cited

U.S. PATENT DOCUMENTS

| | | | |
|---|---|---|---|
| 10,638,938 B1 * | 5/2020 | Tzvieli | ............ A61B 5/748 |
| 2015/0366456 A1 | 12/2015 | Takamori et al. | |
| 2017/0112382 A1 | 4/2017 | Nakata et al. | |
| 2018/0042486 A1 | 2/2018 | Yoshizawa et al. | |

FOREIGN PATENT DOCUMENTS

| | | |
|---|---|---|
| JP | 2015054223 A | 3/2015 |
| JP | 2016190022 A | 11/2016 |
| JP | 6072893 B2 | 1/2017 |
| JP | 2017042386 A | 3/2017 |
| JP | 2019025071 A | 2/2019 |
| KR | 101102624 B1 | 1/2012 |
| WO | 2012039192 A1 | 3/2012 |
| WO | 2016006027 A1 | 1/2016 |

OTHER PUBLICATIONS

Japanese Office Action dated Mar. 15, 2022 (and English translation thereof) issued in Japanese Application No. 2020-031638.

* cited by examiner

FIRST PORTION BEFORE MASSAGE
(PORTION OF DARK CIRCLE UNDER THE EYE)

SECOND PORTION BEFORE MASSAGE (CHEEK PORTION)

FIRST PORTION AFTER MASSAGE
(PORTION OF DARK CIRCLE UNDER THE EYE)

SECOND PORTION AFTER MASSAGE (CHEEK PORTION)

ELECTRONIC DEVICE, CONTROL METHOD FOR THE ELECTRONIC DEVICE, AND STORAGE MEDIUM

This application is based on and claims the benefit of priority from Japanese Patent Application No. 2020-031638, filed on 27 Feb. 2020, the content of which is incorporated herein by reference.

BACKGROUND OF THE INVENTION

Field of the Invention

The present disclosure relates to an electronic device, a control method for the electronic device, and a storage medium.

Related Art

Conventionally, a technique for acquiring biological information such as blood flow of a subject from a video has been known. Japanese Unexamined Patent Application, Publication No. 2016-190022 describes acquiring information relating to a pulse wave of a subject based on luminance information in a video signal, and displaying blood circulation information calculated based on a variation in the pulse wave as a heat map. Japanese Patent No. 6072893 describes that two mutually different parts are simultaneously image-captured from a plurality of parts of a human body in a non-contact state by a single visible light camera, and the pulse wave propagation velocity of the human body is calculated based on the time difference of the pulse wave in the two parts.

SUMMARY OF THE INVENTION

In order to achieve the above object, an electronic device according to an aspect of the present invention includes: a memory; and at least one processor, in which the at least one processor executes a program stored in the memory to perform operation including: acquiring, based on video information of a body in a first video obtained by imaging at least a part of the body, pulse wave information indicating a pulse wave of a first portion of the body and pulse wave information indicating a pulse wave of a second portion different from the first portion of the body; acquiring, based on video information of the body in a second video which is obtained by imaging a part of the body after imaging the first video, pulse wave information indicating a pulse wave of the first portion and pulse wave information indicating a pulse wave of the second portion; and acquiring, based on a relationship between the pulse wave information of the first portion and the pulse wave information of the second portion acquired from the first video, and a relationship between the pulse wave information of the first portion and the pulse wave information of the second portion acquired from the second video, a measurement result indicating a degree of change in blood flow from when imaging the first video to when imaging the second video.

DETAILED DESCRIPTION OF THE INVENTION

Embodiments of the present disclosure will be described below with reference to the drawings.

Summary of the Embodiments

An electronic device 1 according to an embodiment of the present disclosure is a smart mirror configured as a self-supporting mirror that can be carried by a user. The electronic device 1 captures an image of a user as a target person who visually recognizes the mirror. The electronic device 1 acquires blood flow variation before and after a specific action such as a massage based on a video in which the user is image-captured, and displays a hue moving image 63 according to the degree of the blood flow variation. According to such an electronic device 1, it is possible to visually display the blood flow variation before and after a specific action in an easy-to-understand manner.

[System Configuration]

Figure 1:
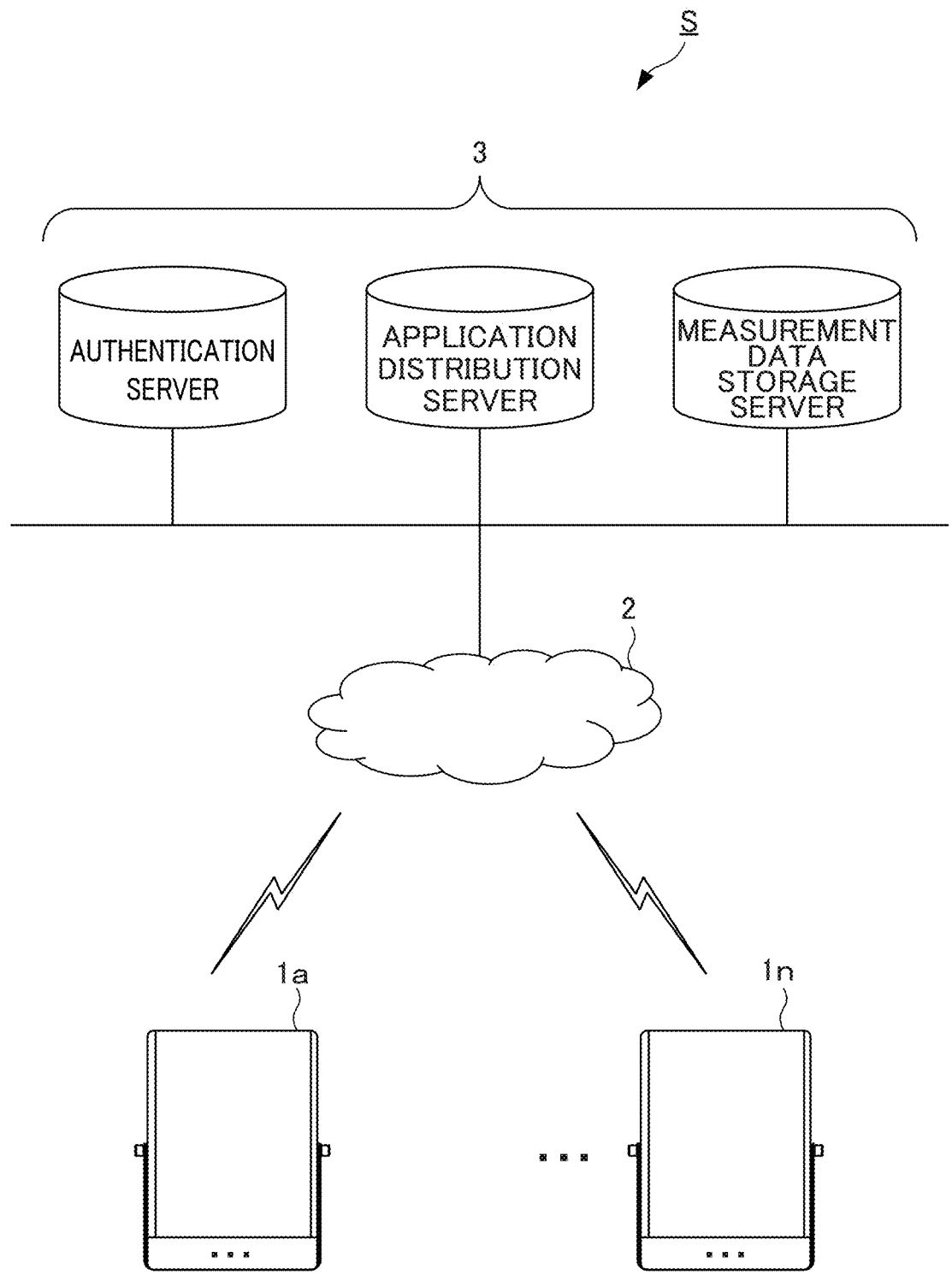
FIG. 1 is a configuration diagram showing a configuration of a measurement system according to an embodiment of the present disclosure.

FIG. 1 is a block diagram showing an overall configuration of a measurement system S including an electronic device 1 according to the present embodiment. As shown in FIG. 1, the measurement system S includes a plurality of electronic devices 1, a network 2, and a server group 3. The number of the electronic devices 1 is not particularly limited, and n-number of electronic devices 1 (n is any natural number) may be included in the display system 1. It should be noted that, in the following description, when the n-number of electronic devices 1 are described without any particular distinction, the letter at the end of the symbol is omitted, and thus these devices are simply referred to as "electronic device 1".

The electronic device 1 is a measurement device that measures blood flow variation of a user from a video and displays a measurement result. The electronic device 1 is connected to each server included in the server group 3 so as to be able to communicate with each other via the network 2.

The network 2 is realized by, for example, the Internet, a LAN (Local Area Network), any of cellular telephone networks, or a combination thereof.

The server group 3 includes various servers that cooperate with the electronic device 1. For example, the server group 3 includes an authentication server for authenticating a user of the electronic device 1. Furthermore, for example, the server group 3 includes an application distribution server that distributes application software for realizing the functions of the electronic device 1. Furthermore, for example, the server group 3 includes a measurement data storage server that stores profile information of the user, which is information including setting information related to the user, a usage history of the electronic device 1 by the user, and the like.

It should be noted that the measurement system S shown in FIG. 1 is merely an example, and a server having another function may be included in the server group 3. Furthermore, a plurality of servers included in the server group 3 may be implemented by a separate server device, or may be implemented by a single server device.

[Exterior Appearance Configuration]

Figure 2:
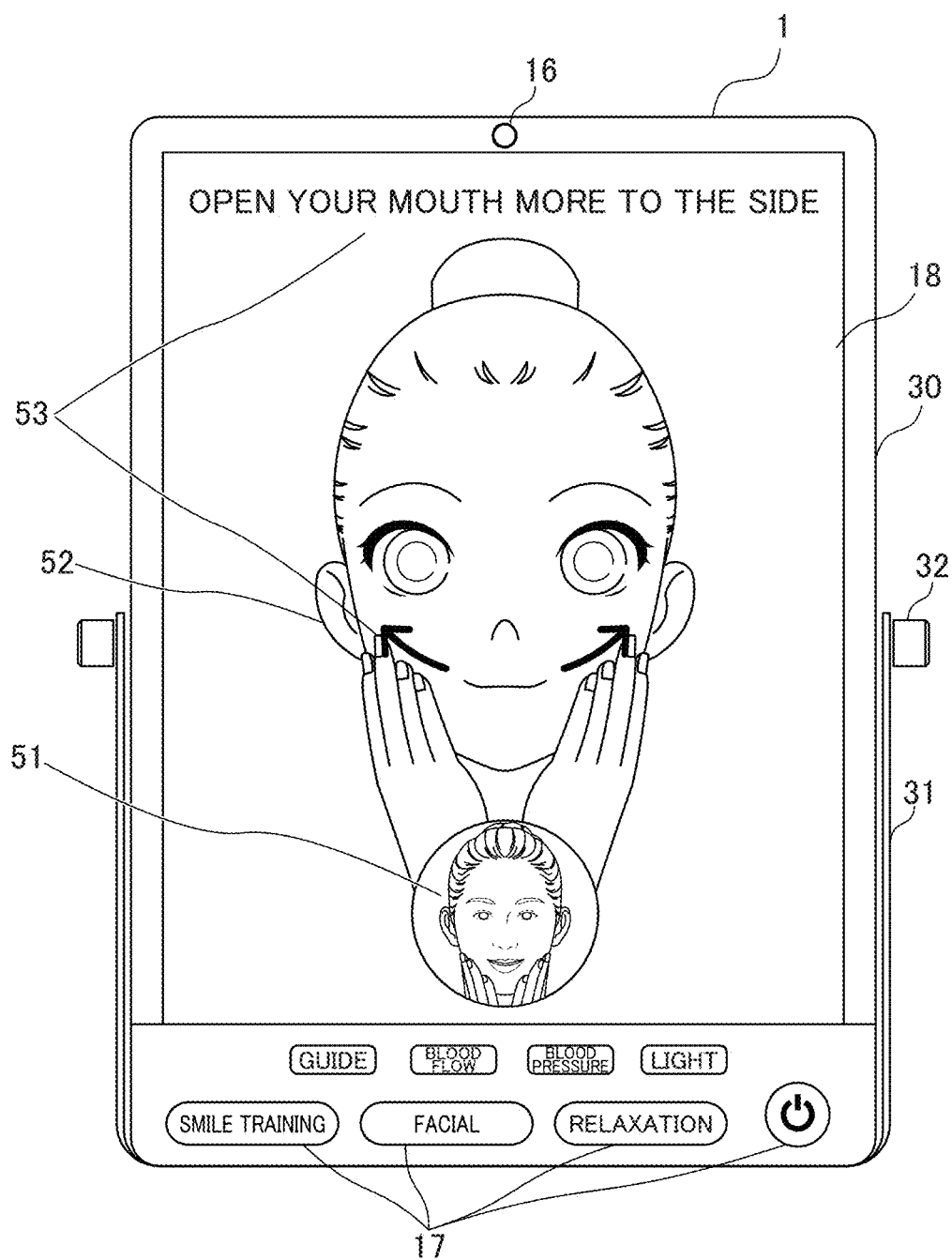
FIG. 2 is a configuration diagram showing an exterior appearance configuration of a front surface of an electronic device according to an embodiment of the present disclosure.
Figure 3A:
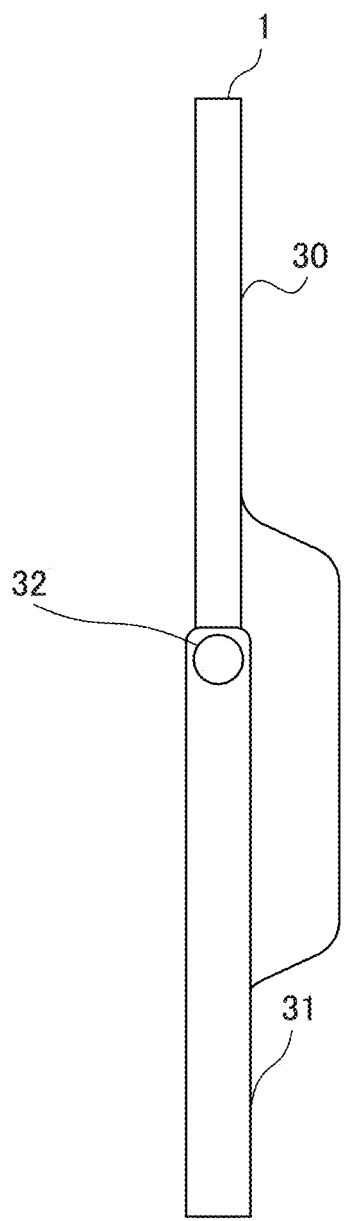
FIG. 3A is a configuration diagram showing an exterior appearance configuration of a side surface of an electronic device according to an embodiment of the present disclosure.
Figure 3B:
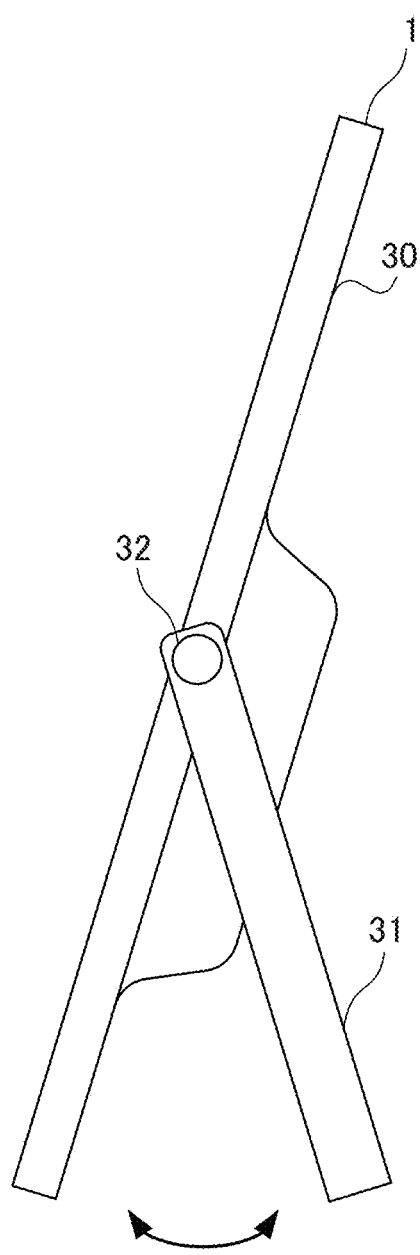
FIG. 3B is a configuration diagram showing an exterior appearance configuration of a side surface of an electronic device according to an embodiment of the present disclosure.

FIG. 2 is a configuration diagram showing an exterior appearance configuration of a front surface of the electronic device 1 according to an embodiment of the present disclosure. Furthermore, FIG. 3A and FIG. 3B are each a block diagram showing an exterior appearance configuration of a side surface of the electronic device 1. The size of the front surface of the electronic device 1 is, for example, A4 size defined by ISO (International Organization for Standardization) 216, which is an internationally recognized standard.

As shown in FIG. 2, FIG. 3A and FIG. 3B, the electronic device 1 includes a main body portion 30, a leg portion 31, and a hinge portion 32. The main body portion 30 is a portion including the display unit 18 and other hardware to be described later with reference to FIG. 4. Furthermore, the leg portion 31 and the hinge portion 32 are members for allowing the electronic device 1 to stand freely. The leg portion 31 is rotatably supported with respect to the main body portion 30 by the hinge portion 32.

As shown in FIG. 3A, when carrying the electronic device 1, it is possible for the user to carry the electronic device 1 in a non-bulky form in which the side surface of the main body portion 30 is aligned with the side surface of the leg portion 31. On the other hand, as shown in FIG. 3B, when the user installs and uses the electronic device 1 on a desk or the like, it is possible to install the electronic device 1 independently by rotating the leg portion 31 around the hinge portion 32 as a center point. It should be noted that, in order to allow the electronic device 1 to stand freely, the hinge portion 32 has a mechanism for holding in a state where the leg portion 31 is kept at a predetermined angle.

The main body portion 30 includes the display unit 18 as described above. The display unit 18 is a portion for displaying these various kinds of information to the user by displaying various kinds of information. The display unit 18 displays, for example, a user image (corresponding to a user image 51 in the figure) which is a real image of the user captured by the imaging unit 16 as a subject, an avatar image (corresponding to an avatar image 52 in the figure) which is a substitute image for the user, and a guide image (corresponding to a guide image 53 in the figure) which is auxiliary information for performing guidance. Furthermore, in this case, the guide image is composited with the avatar image and displayed in a superimposed manner on the display unit 18.

The user can grasp these various pieces of information at a time by visually recognizing the display unit 18. It should be noted that the display of the display unit 18 as described above has a sense of unity suitable for the user to visually recognize without a visual gap.

As shown in FIG. 2, the electronic device 1 further includes an imaging unit 16, an input unit 17, and the display unit 18, as an exterior appearance configuration.

The imaging unit 16 is a camera for capturing a user facing the display unit 18 as a subject during the use of the electronic device 1. The imaging unit 16 is disposed at a position where the user image 51 including the face of the user directly facing the display unit 18 can be captured. For example, as shown in the drawing, the imaging unit 16 is disposed on the front surface of the main body portion 30 and on the upper portion of the display unit 18.

The input unit 17 is a unit for receiving an operation input by a user. The input unit 17 is realized by a plurality of buttons, for example. In the drawing, as an example, buttons for switching to various modes such as small face beauty treatment, smile training, and recording of biometric information, and a button for switching on/off the power of the electronic device 1 are illustrated.

The external structure of the electronic device 1 has been described above. However, this structure is merely an example, and the external structure of the electronic device 1 is not limited to this example.

For example, the electronic device 1 may further include a light emitting unit that emits light to illuminate the user facing the display unit 18. The light emitting unit illuminates the user by adjusting the illuminance and color components. Therefore, the electronic device 1 functions as a mirror with illumination. A plurality of light emitting units may be provided. Furthermore, the light emitting unit may be disposed at the upper portion or the lower portion of the display unit 18, or may be disposed over the entire periphery of the display unit 18.

Furthermore, for example, the number and arrangement of the input units 17 may be changed. Furthermore, for example, a part of the display unit 18 may be configured as a touch screen, and the input unit 17 and the display unit 18 may be integrally configured.

[Hardware Configuration]

Figure 4:
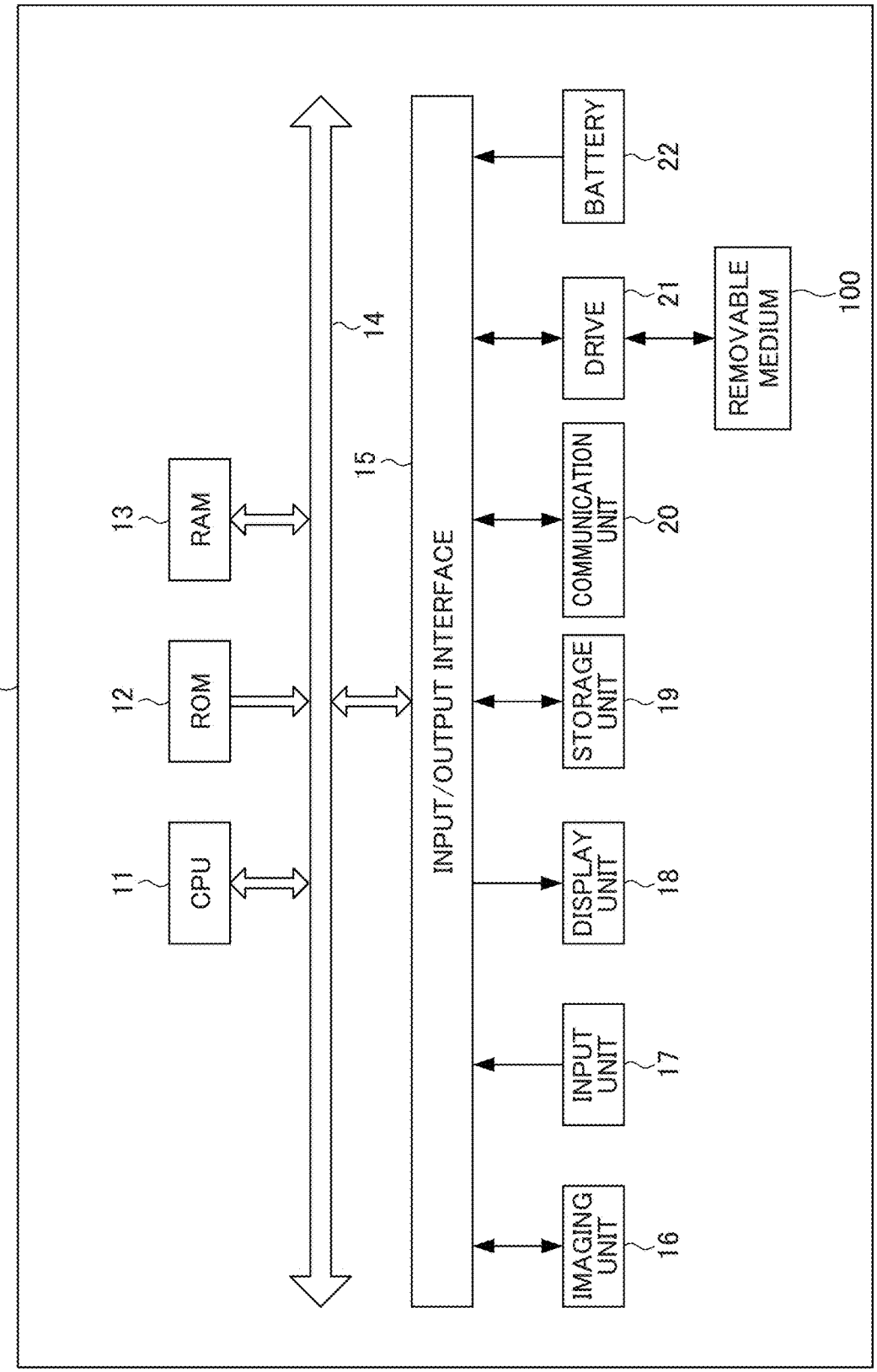
FIG. 4 is a block diagram showing a hardware configuration of an electronic device according to an embodiment of the present disclosure.

FIG. 4 is a block diagram illustrating a hardware configuration of the electronic device 1. As illustrated in FIG. 4, the electronic device 1 includes a central processing unit (CPU) 11 which is a processer, a read only memory (ROM) 12, a random access memory (RAM) 13, a bus 14, an input/output interface 15, an imaging unit 16, an input unit 17, a display unit 18, a storage unit 19, a communication unit 20, a drive 21 and a battery 22.

The CPU 11 executes various processings according to a program recorded in the ROM 12, or a program loaded in the RAM 13 from the storage unit 19.

Data or the like necessary for the CPU 11 to execute various processings, is also suitably stored in the RAM 13.

The CPU 11, the ROM 12, and the RAM 13 are connected to each other through the bus 14. In addition, the input/output interface 15 is also connected to the bus 14. The imaging unit 16, the input unit 17, the display unit 18, the storage unit 19, the communication unit 20, the drive 21 and the battery 22 are connected to the input/output interface 15.

Although not illustrated, the imaging unit 16 includes an optical lens unit and an image sensor. The optical lens unit includes a lens such as, for example, a focus lens, a zoom lens, or the like that collects light in order to photograph a subject. The focus lens is a lens that forms a subject image on a light receiving surface of the image sensor. The zoom lens is a lens that causes a focal length to be freely changed within a certain range. Further, a peripheral circuit for adjusting setting parameters such as focus, exposure, white balance, and the like is installed in the imaging unit 16 if necessary.

The image sensor is configured of a photoelectric conversion element, an analog front end (AFE), or the like. The photoelectric conversion element, for example, is configured of a complementary metal oxide semiconductor (CMOS) type photoelectric conversion element or the like. The subject image is incident on the photoelectric conversion element from the optical lens unit. Then, the photoelectric conversion element performs photoelectric conversion (imaging) with respect to the subject image, accumulates an image signal for a constant time, and sequentially supplies the accumulated image signals to the AFE, as an analog signal. The AFE executes various signal processings such as analog/digital (A/D) conversion processing, with respect to the analog image signal. A digital signal is generated by the various signal processings, and is output as an output signal from the imaging unit 16. Such output signal from the imaging unit 16 is appropriately supplied to the CPU 11 or the like.

The input unit 17 includes various types of buttons, microphones or the like, and inputs various types of information in accordance with an instruction manipulation or an instruction voice of the user.

The display unit 18 includes a liquid crystal display or the like, and displays an image corresponding to image data output from the CPU 11.

The storage unit 19 includes a semiconductor memory such as a dynamic random access memory (DRAM) and stores various types of data.

In the communication unit 21, the CPU 11 performs communication control for performing communication with other devices (for example, the servers included in the server group 3) via the network 2.

The drive 21 is constituted by an interface onto which a removable medium 100 can be loaded. The removable medium 100 including a magnetic disk, an optical disk, a magneto-optical disk, a semiconductor memory or the like is properly loaded onto the drive 21. The removable medium 100 stores a program for executing a composition display process to be described later or various types of data such as image data. The program or various types of data such as image data read from the removable medium 100 by the drive 21 is installed in the storage unit 19 if necessary.

The battery 22 supplies power to each part of the device and and is configured to be rechargeable when connected to an external power source. When the electronic device 1 is not connected to an external power supply, the electronic device 1 operates by the power of the battery 22.

The electronic device 1 may further include another hardware in addition to the hardware described above. For example, the electronic device 1 includes a lamp, a speaker, a vibration motor, or the like, and may include an output section that outputs light, a sound, or a vibration signal.

[Functional Configuration]

Figure 5:
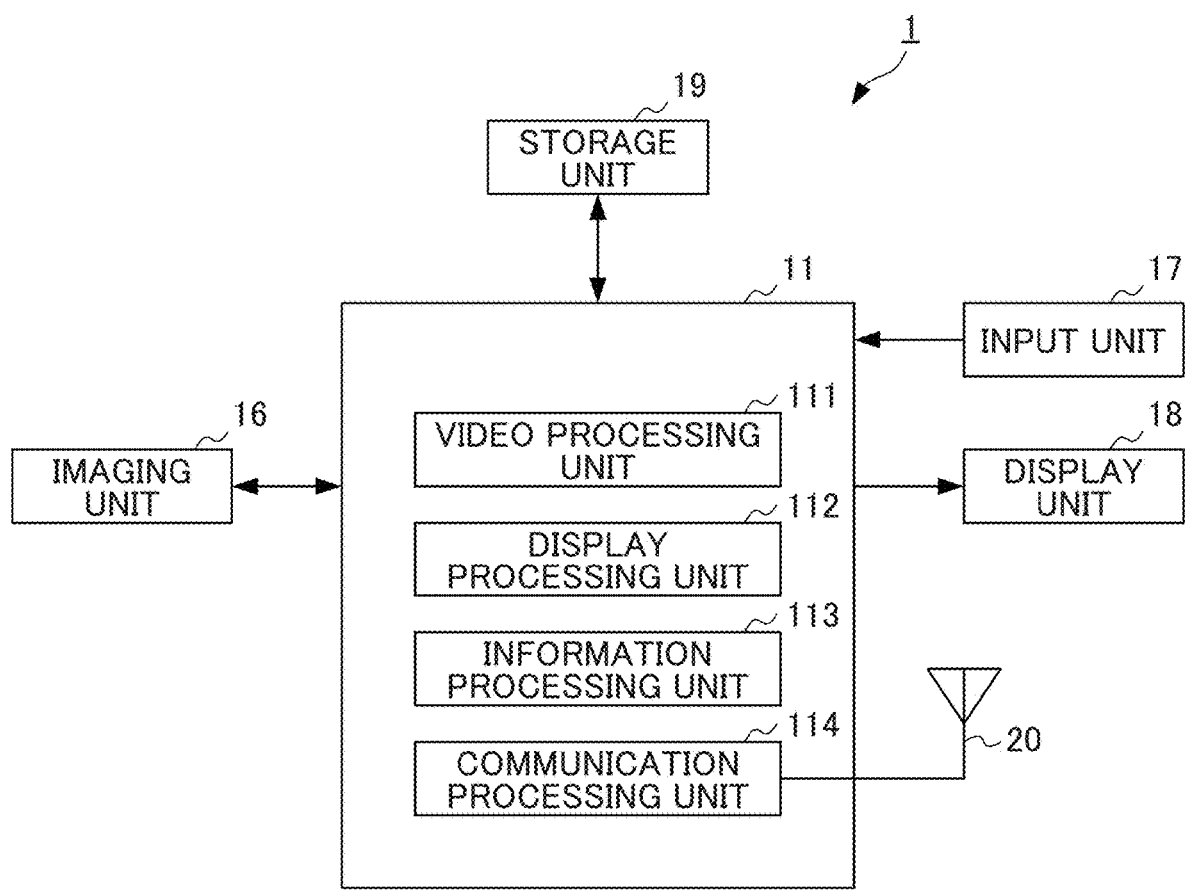
FIG. 5 is a functional block diagram showing a functional configuration for executing measurement processing among the functional configurations of the electronic device according to the embodiment of the present disclosure.

FIG. 5 is a functional block diagram showing a functional configuration for executing measurement processing among the functional configurations of the electronic device 1. The measurement processing refers to a series of processing in which the electronic device 1 displays the measurement result based on the change in the biological information value acquired from the user.

First, the storage unit 19 for storing various kinds of information will be described. The storage unit 19 stores various types of data relating to guidance in the display processing, various types of data relating to avatars as substitutes for the real image of the user, information for performing measurement, information for displaying the measurement result, information indicating the measurement result, and the like. It should be noted that the above-described various types of data may be stored only in the storage unit 19, or may be stored as appropriate in the removable medium 100 by the drive 21. Furthermore, each piece of information may be stored as appropriate in the measurement data storage server or the like included in the server group 3.

Next, each functional block for executing the measurement processing will be described. As shown in FIG. 5, the video processing unit 111, the display processing unit 112, the information processing unit 113, and the communication processing unit 114 function in the CPU 11 as a control unit.

The video processing unit 111 analyzes a video including the user as a subject captured by the imaging unit 16, thereby acquiring information about the user (hereinafter referred to as "subject information"). Examples of the subject information include coordinates indicating the position of each portion in the face or the like of the user image 51, the color of each portion in the face or the like of the user image 51, biometric information indicating the state of the user (sometimes referred to as vital data), or the like. Since the measurement is performed based on the information (video) acquired by the imaging unit 16, the biometric information can be sequentially acquired without touching the user.

Coordinate information as a precondition for performing measurement processing will be described. The coordinate information includes, for example, information for defining each coordinate system, such as an imaging coordinate system that is a coordinate system for an image captured by the imaging unit 16, a display unit coordinate system that is a coordinate system for a display surface of the display unit 18, and information indicating a corresponding relationship for converting coordinates in each coordinate system to coordinates in another coordinate system. Each functional block can perform display processing by transforming coordinates in each coordinate system based on the corresponding relationship of coordinates in each coordinate system. The corresponding relationship of these coordinate systems is set by performing calibration with correction of the corresponding relationship by, for example, the direction adjustment of an imaging lens in the imaging unit 16, or the adjustment of the zoom ratio, etc., at the time of manufacturing the electronic device 1. For example, the adjustment of the zoom ratio is performed using either or both of so-called optical zoom performed by the adjustment of a lens position of the imaging unit 16 and a so-called digital zoom in the image processing.

The display processing unit 112 performs control to display a moving image as a display video. With such a configuration, the blood flow variation can be visualized dynamically, and the difference between before and after a specific action can be displayed in an easy-to-understand manner. The moving image according to the present embodiment is the hue moving image 63 representing the measurement result by a hue (refer to FIG. 8). The hue moving image 63 shows a state in which a specific portion (first portion) is divided into small areas in the shape of a square, and the blood flow variation is represented by a change in hue for each small area. The specific portion is, for example, a part of the face. An example of the hue moving image 63 will be described later.

Furthermore, the display processing unit 112 also performs composition processing for compositing a guide image and an avatar image. For example, the display processing unit 112 controls the display unit 18 to display a mirror image of the user or an image (e.g., avatar) corresponding to the user. For example, the display processing unit 112 executes processing for switching between a first display mode in which a user image is displayed as a main image and in which an avatar image and a guide image are composited and the resulting composite image is displayed as a sub image, and a second display mode in which the user image is displayed as a sub image and in which the avatar image and the guide image are composited and the resulting composite image is displayed as a main image. As shown in FIG. 2, the avatar image and the guide image, which are composite images, can be displayed in a large size at the center of the screen as a main image, and the user image can be displayed in a smaller size at the bottom of the screen or the like as a sub image. Conversely, the user image may be displayed in a larger size at the center of the screen as a main image, and the avatar image and the guide image, which are composite images, may be displayed in a smaller size at the bottom of the screen or the like as a sub image.

The information processing unit 113 performs control such as setting relating to measurement processing and display processing. The information processing unit 113 acquires a measurement result indicating a change in blood flow based on data analysis of the video processing unit 111. The acquisition of the measurement result indicating the change in blood flow by the information processing unit 113 will be described later.

Furthermore, the information processing unit 113 acquires application software for performing display processing from the application distribution server included in the server group 3, and operates the application software. In addition, the information processing unit 113 receives selection of any guidance content from the user who has referred to the menu displayed on the display unit 18 via the input unit 17 or the like. For example, the selection of "small face beauty treatment" is received. In response, the display processing is performed for guidance in relation to small face beauty treatment. It should be noted that the small face beauty treatment means, for example, that a user performs lymph massage or the like on the user's face by himself/herself to reduce the swelling of the face by massage to flow lymph.

The communication processing unit 114 communicates with, for example, an authentication server included in the server group 3. Thus, the user performing the display processing is authenticated. Furthermore, the communication processing unit 114 updates the profile information of the user in the display processing by communicating with, for example, the measurement data storage server included in the server group 3.

[Analysis of Video Data]

Figure 6:
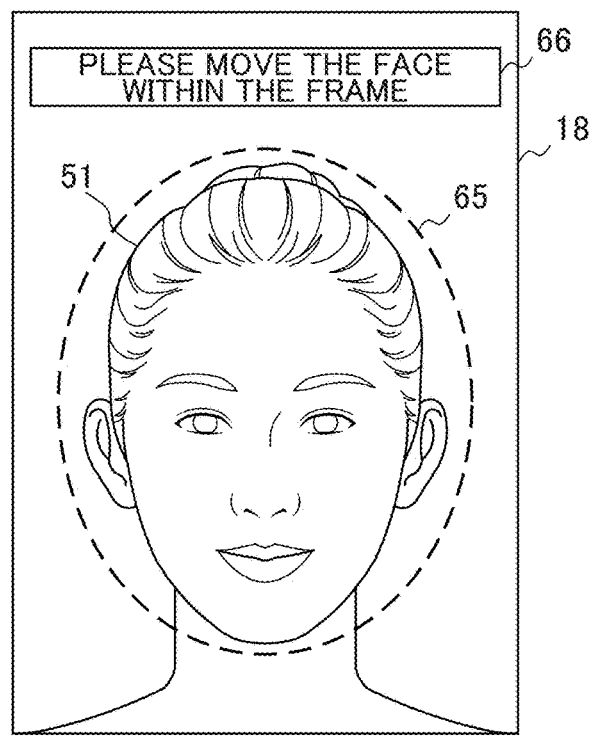
FIG. 6 is a diagram showing an example of a guide image displayed on a display unit of an electronic device according to an embodiment of the present disclosure.

First, the acquisition of video data analyzed by the video processing unit 111 will be described. FIG. 6 is a diagram showing an example of a guide image displayed on the display unit 18 of the electronic device 1 according to the embodiment of the present disclosure. As shown in FIG. 6, the display processing unit 112 executes processing of displaying a guide frame 65 of the face displayed by a figure surrounded by a broken line on the display unit 18. In addition, the display processing unit 112 displays a text 66 telling the user to move the user's face in the guide frame 65 of the face together with the guide frame 65 of the face. For example, the text 66 "Please move the face within the frame" is displayed on the display unit 18.

The video processing unit 111 performs processing relating to face tracking such as pattern matching of contours and regions, skin color identification, and the like, thereby recognizing the contours of the face, the positions of eyes, and regions of the skin, and detecting predetermined regions such as the forehead, cheek, jaw, and neck. For example, a face contour and an eye position are detected from the user image 51 in the video image, and a plurality of regions such as forehead, an eyelid, a cheek, a nasal periphery, a lip periphery, a jaw, a neck, and a low-necked portion are automatically recognized based on the relative positions thereof. Furthermore, the video processing unit 111 detects the coordinates and the skin color of the user of each of the detected regions, and the angle of the face of the user image 51, i.e., the direction of the user's face.

The video processing unit 111 uses the property that the hemoglobin in the blood absorbs green light well to extract the pulse wave from the video, and acquires the biological information about the blood flow such as the pulse and the pulse wave. The wavelength of the green signal is generally considered to be 495-570 nm, and hemoglobin has a high absorption coefficient around 550-660 nm. When the blood flow rises, the amount of blood increases on the skin surface and the amount of hemoglobin per unit time increases, so that more green signals are absorbed by the hemoglobin than before the blood flow rises. Therefore, the luminance of the green signal detected when the blood flow rises decreases. It should be noted that, when an imaging device of the imaging unit 16 converts the light into luminance, an RGB filter is provided in front of the imaging device, and the luminance value of each pixel for the respective RGBs is calculated. In this case, the light passing through the green filter becomes the luminance value. Even if the sensitivity of the imaging device is flat with respect to the wavelength, since the wavelength band can be narrowed down accurately to some extent by the filter described above, it is possible to detect the green signal.

The video processing unit 111 acquires pulse wave information based on the luminance information included in the video information of a body in the video. More specifically, the video processing unit 111 acquires the pulse wave information from the temporal change in luminance of the green signal by acquiring the luminance of the green signal for each unit time. It should be noted that the unit time is, for example, a frame rate of the moving image, and it is possible to acquire the luminance of the green signal for each image which is consecutively present in time to constitute the video.

In the present embodiment, in order to make it easier to grasp the increase of the blood flow in a sensory manner, conversion processing is performed so that the luminance value becomes high when the blood flow rises. More specifically, when the luminance of the green signal is detected using an image sensor of the output of 8 bits of each RGB color, a numerical value obtained by subtracting a detected luminance value of the green signal from the maximum value 255 of the luminance value is used as "converted luminance" for comparison processing. What is simply described as the converted luminance hereinafter is information about the luminance subjected to such conversion processing.

In order to compare the states of the blood flow before and after the event of the user, the electronic device 1 acquires a first video by imaging the user before the event and acquires a second video by imaging the user after the event.

The event is, for example, a massage for promoting blood flow, various cosmetic treatments such as application of skin cream promoting blood circulation, or various actions in which a change in blood flow is predicted such as exercise such as sports or relaxation. Therefore, the time difference between the measurement timing before the event and the measurement timing after the event may vary from about 5 minutes to several tens of minutes, as in the case of massage, or from several days to several months, as in the case of applying skin cream daily for a long period of time.

Figure 7:
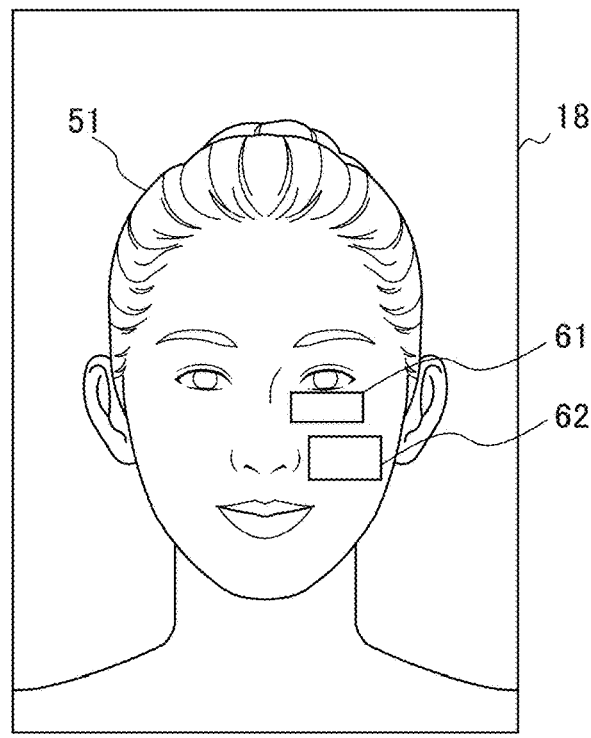
FIG. 7 is a diagram showing an example of a first portion and a second portion displayed on a display unit of an electronic device according to an embodiment of the present disclosure.

If the imaging status or user status changes before and after the event, the effect of the event may not be accurately measured. For this reason, in the present embodiment, measurement is performed for at least at two points, i.e., the first portion 61 which is a measurement target and the second portion 62 which is measured for reference in order to eliminate the cause of measurement error. FIG. 7 is a diagram showing an example of the first portion 61 and the second portion 62 displayed on the display unit 18 of the electronic device 1 according to an embodiment of the present disclosure. In the example shown in FIG. 7, the portion in which dark circles occur under the eye is set as the first portion 61, and a part of the cheek is set as the second portion 62.

Figure 8:
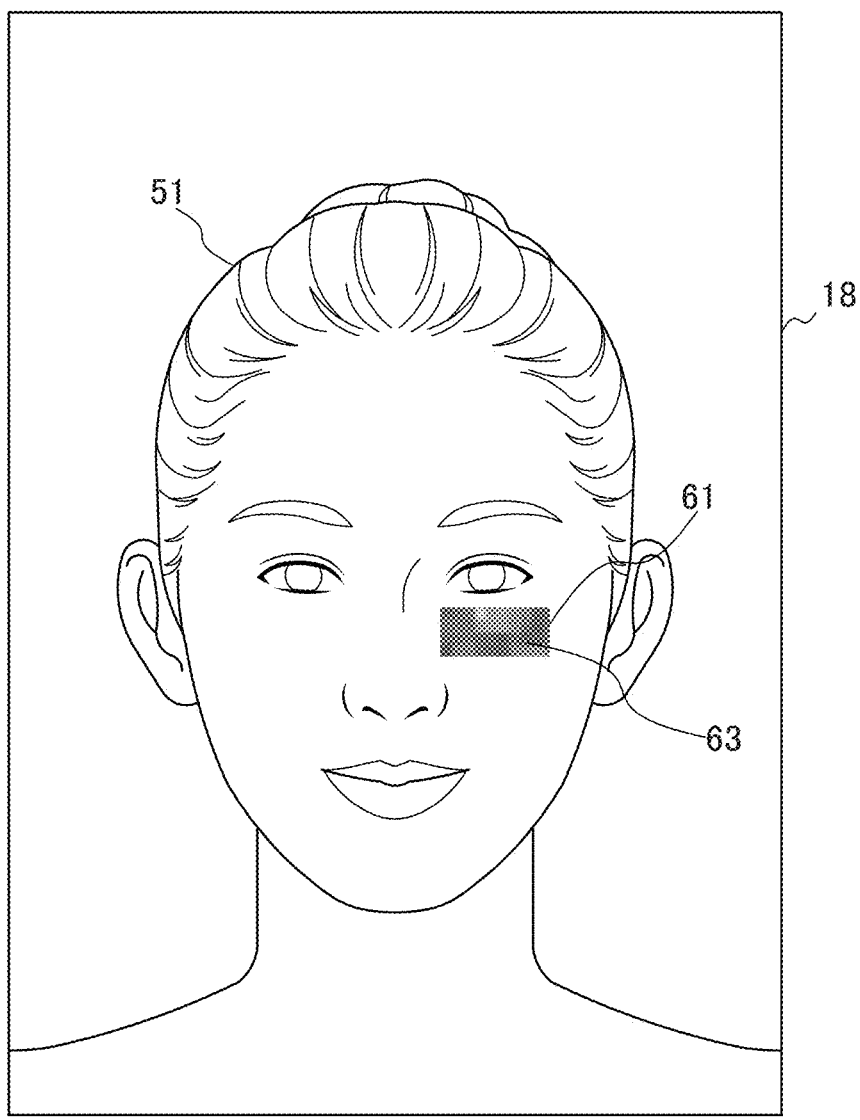
FIG. 8 is a diagram showing an example of a measurement result displayed on a display unit of an electronic device according to an embodiment of the present disclosure.

FIG. 8 is a diagram showing an example of a measurement result displayed on the display unit 18 of the electronic device 1 according to the embodiment of the present disclosure. In the example shown in FIG. 8, the hue moving image 63 expressing the measurement result in color is displayed in a superimposed manner on the first portion 61 in which dark circles occur under the user's eyes.

In order to generate a mosaic hue moving image 63 visually displaying the state of the user's blood flow, the video processing unit 111 divides the first portion 61 in the video into a plurality of small regions, and acquires a temporal change in luminance for each small region. For example, when the lower part of an eye is set as the first portion 61, the lower part of the eye is divided into 30×30 mosaic small areas. Thereafter, the temporal change in luminance of the green signal is calculated for each small area. The small area is composed of at least one pixel. When the small area is composed of a plurality of pixels, the average value of the luminance of the plurality of pixels may be the luminance of the small area.

The hue moving image 63 displays a color corresponding to the value of the luminance of the green signal at a certain point in time in each small area. Since the luminance of the green signal varies depending on the blood flow, the color displayed in each small area also changes with time. The display processing unit 112 generates an image in which a color corresponding to the value of the luminance is set in each of the regions at a certain point in time. By temporally continuing the images thus generated, the hue moving image 63 whose color changes in a mosaic pattern is generated.

In the example shown in FIG. 8, the hue moving image 63 is not displayed in the second portion 62. This is because the second portion 62 is a portion to be measured for reference.

Next, analysis processing using the second portion 62 will be described with reference to examples. In the present examples, a subject is a person who actually has blue dark circles under the eyes, and the event is that the subject himself/herself performs a thumb pushing massage for improving the dark circles under the eyes.

Figure 9:
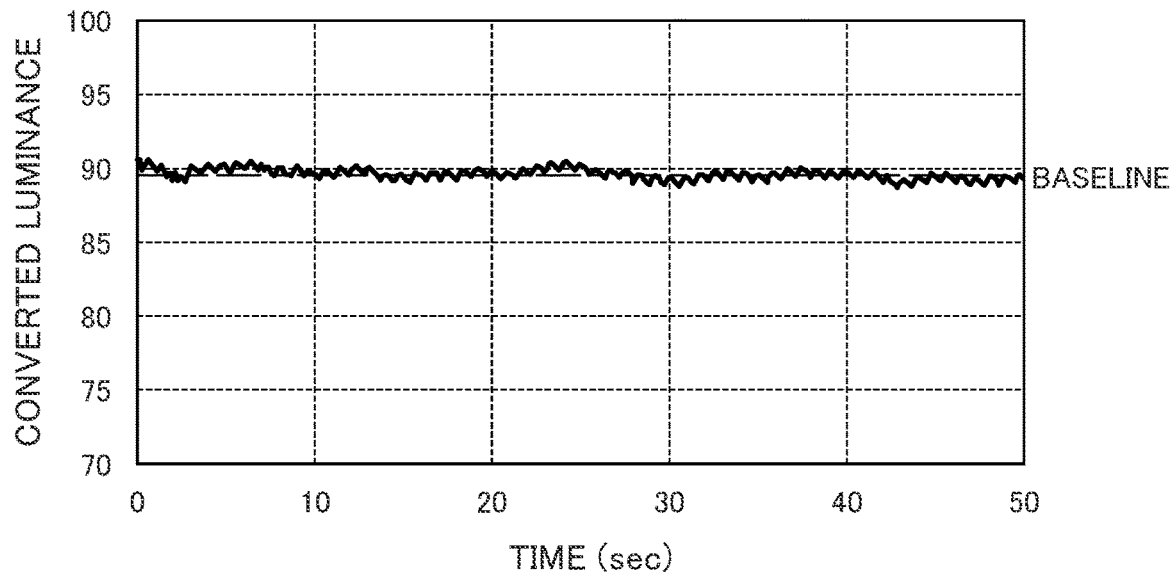
FIG. 9 is a graph showing a temporal change in a converted luminance of the first portion before a massage measured by an electronic device according to an embodiment of the present disclosure.
Figure 10:
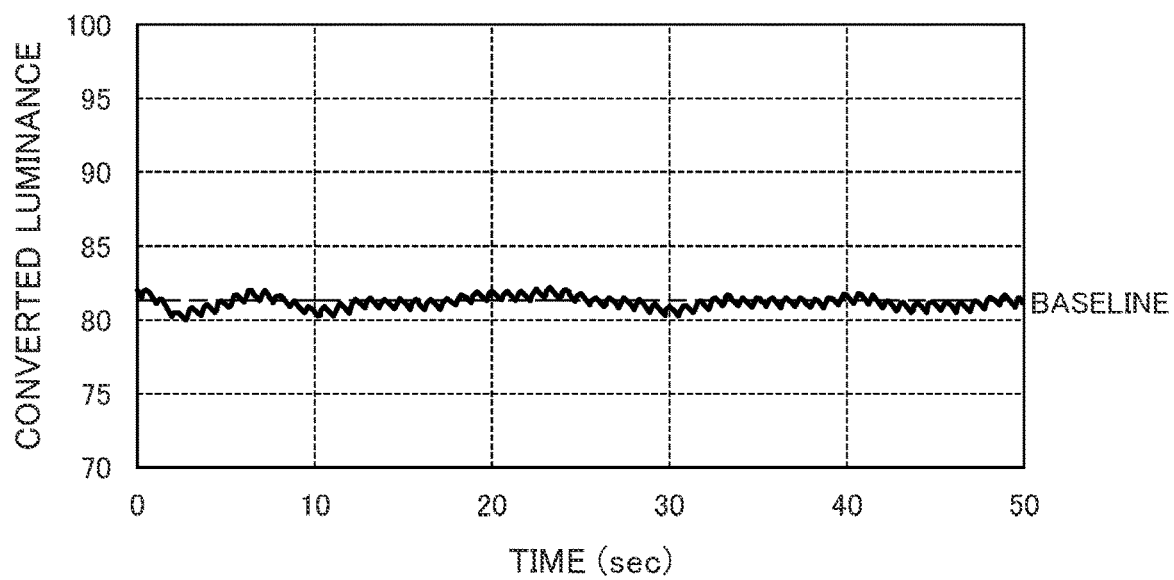
FIG. 10 is a graph showing a temporal change in the converted luminance of the second portion before the massage measured by an electronic device according to an embodiment of the present disclosure.
Figure 11:
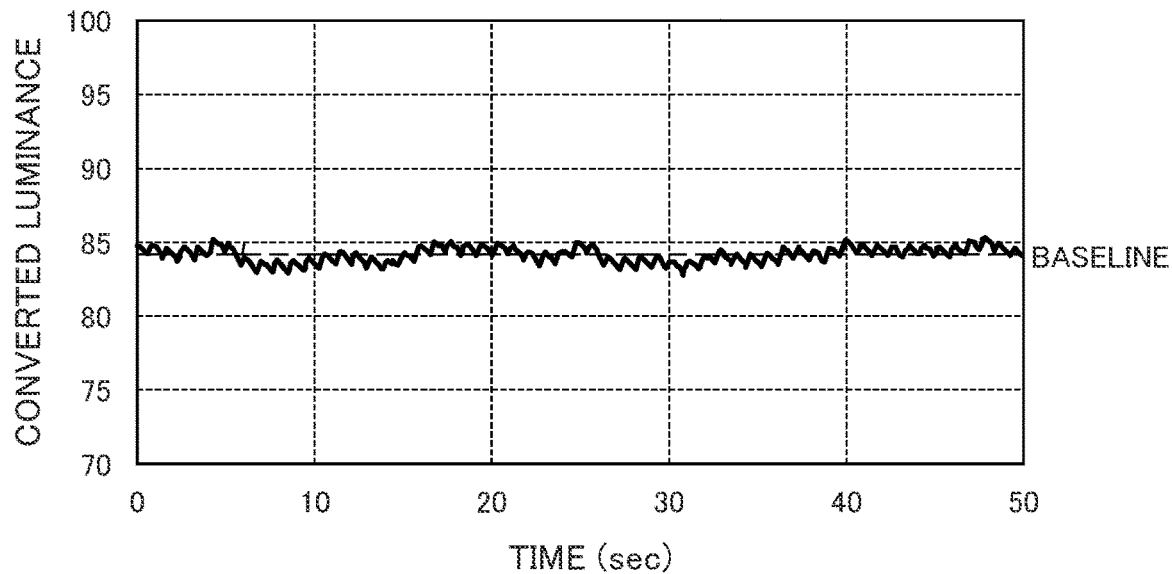
FIG. 11 is a graph showing a temporal change in the converted luminance of the first portion after the massage measured by an electronic device according to an embodiment of the present disclosure.
Figure 12:
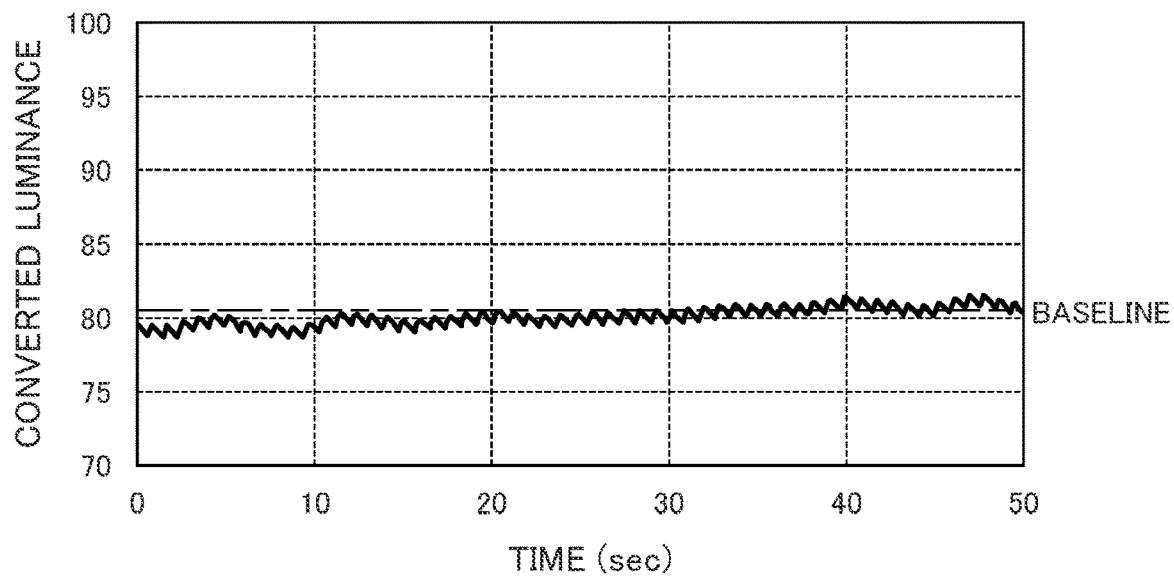
FIG. 12 is a graph showing a temporal change in the converted luminance of the second portion after the massage measured by an electronic device according to an embodiment of the present disclosure.

FIG. 9 is a graph showing a temporal change in the converted luminance of the first portion 61 before the massage measured by the electronic device 1 according to the embodiment of the present disclosure. In FIG. 9, the temporal change of the representative value of the luminance at the first portion 61 in the first video before the event is shown. FIG. 10 is a graph showing a temporal change in the converted luminance of the second portion 62 before the massage measured by the electronic device 1 according to the embodiment of the present disclosure. FIG. 10 shows the temporal change of the representative value of the luminance in the second portion 62 in the first video before the event. FIG. 11 is a graph showing a temporal change in the converted luminance of the first portion 61 after massage measured by the electronic device 1 according to the embodiment of the present disclosure. FIG. 11 shows the temporal change of the representative value of the luminance in the first portion 61 in the second video after the event. FIG. 12 is a graph showing a temporal change in the converted luminance of the second portion 62 after the massage measured by the electronic device 1 according to the embodiment of the present disclosure. FIG. 12 shows the temporal change of the representative value of the luminance in the second portion 62 in the second video after the event.

It should be noted that the converted luminance of the green signal shown in FIGS. 9 to 12 reflects the luminance of the green signal at a plurality of locations in the region to be measured, and is calculated by various methods such as most frequent value, median value, and average value. In the present embodiment, the temporal change of the average value of the luminance of the green signal of all the pixels of the measured portion is acquired as the representative pulse wave information.

The temporal changes of the representative values before and after a thumb pushing massage for improving dark circles are compared between the first portion 61 and the second portion 62, respectively. The baseline indicating the average value of the pulse wave at a predetermined time before the event drops by about 5. On the other hand, in the second portion 62 as shown in FIGS. 10 and 12, the baseline, which is the average value of the whole, did not change substantially.

Figure 13:
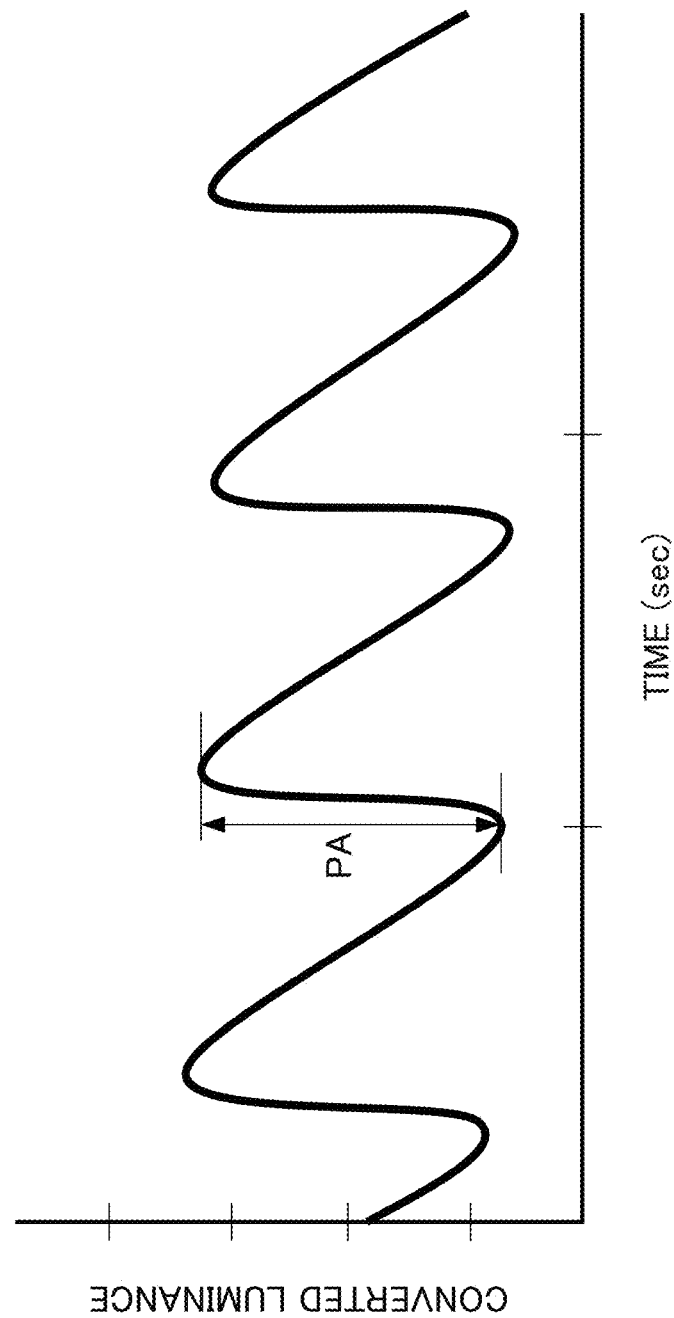
FIG. 13 is a graph schematically showing the amplitude of a pulse wave measured by an electronic device according to an embodiment of the present disclosure.

Incidentally, the pulse wave has an amplitude. FIG. 13 is a diagram schematically showing the amplitude PA (Pulse Amplitude) of the pulse wave measured by the electronic device 1 according to an embodiment of the present disclosure. As shown in FIG. 13, the pulse wave analyzed from the video shows a periodic waveform showing a waveform within a range of a constant amplitude PA. The amplitude PA of this pulse wave indicates the difference between the adjacent maximum and minimum values of the pulse wave signal. It should be noted that the range for acquiring the amplitude PA is preferably a region in which the amplitude is stable without abnormal values. For example, when an abnormal value exceeding a preset threshold value is detected, the pulse wave information is acquired so that the abnormal value is excluded. Alternatively, it is also possible to display a message that the video could not be appropriately acquired at the time of capturing, and appropriate pulse wave information may be acquired by performing capturing of the video again. Alternatively, the pulse wave after a predetermined time from the start of capturing may be used for the calculation of the amplitude. Alternatively, the amplitude may be calculated by excluding the abnormal value from the pulse wave acquired within a predetermined time. As described above, various methods can be applied to the calculation of the amplitude.

Figure 14:
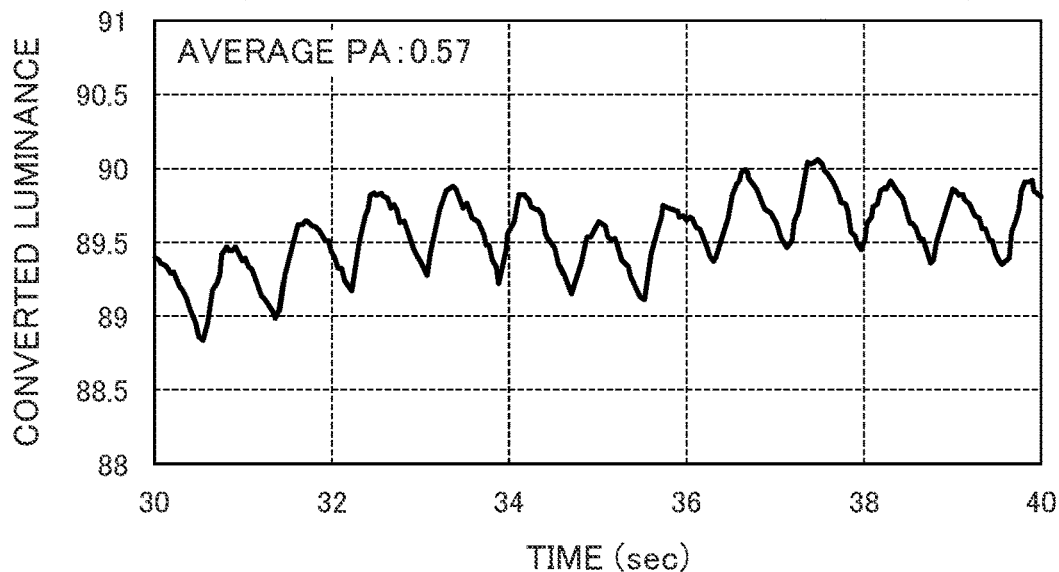
FIG. 14 is a graph showing an amplitude of the first portion before massage measured by an electronic device according to an embodiment of the present disclosure.
Figure 15:
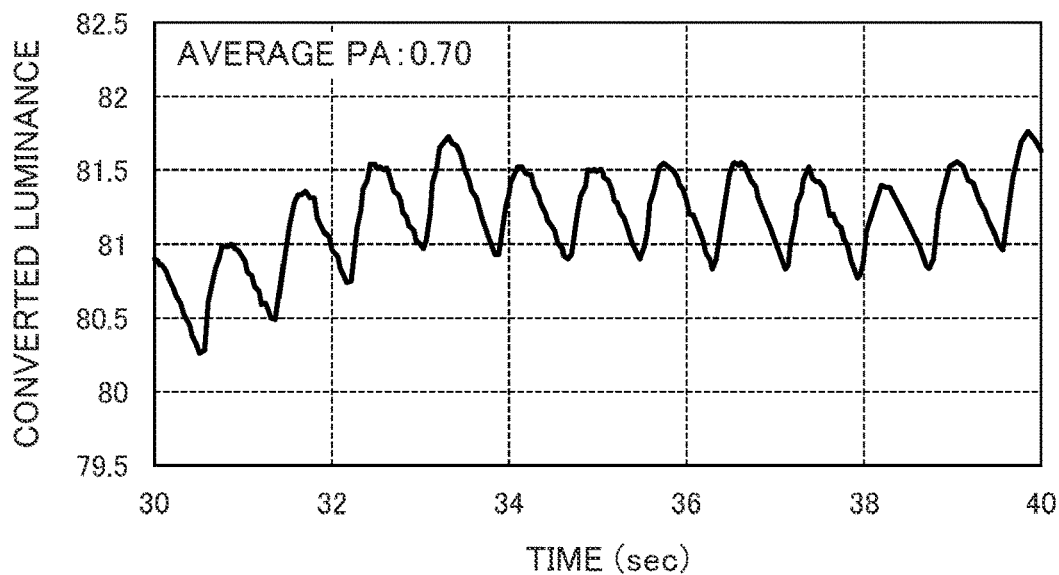
FIG. 15 is a graph showing an amplitude of the second portion before massage measured by an electronic device according to an embodiment of the present disclosure.
Figure 16:
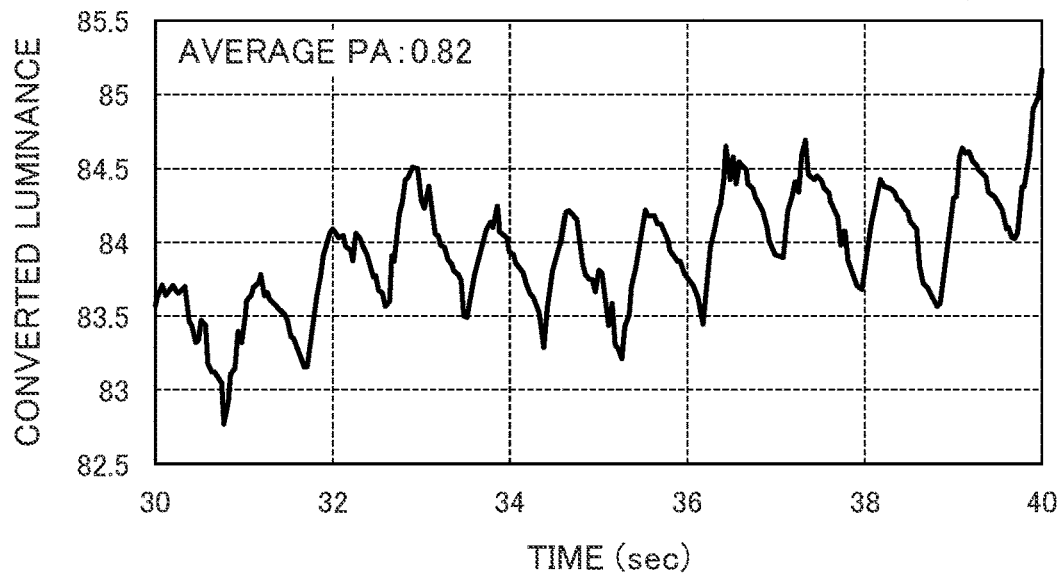
FIG. 16 is a graph showing an amplitude of the first portion after massage measured by an electronic device according to an embodiment of the present disclosure.
Figure 17:
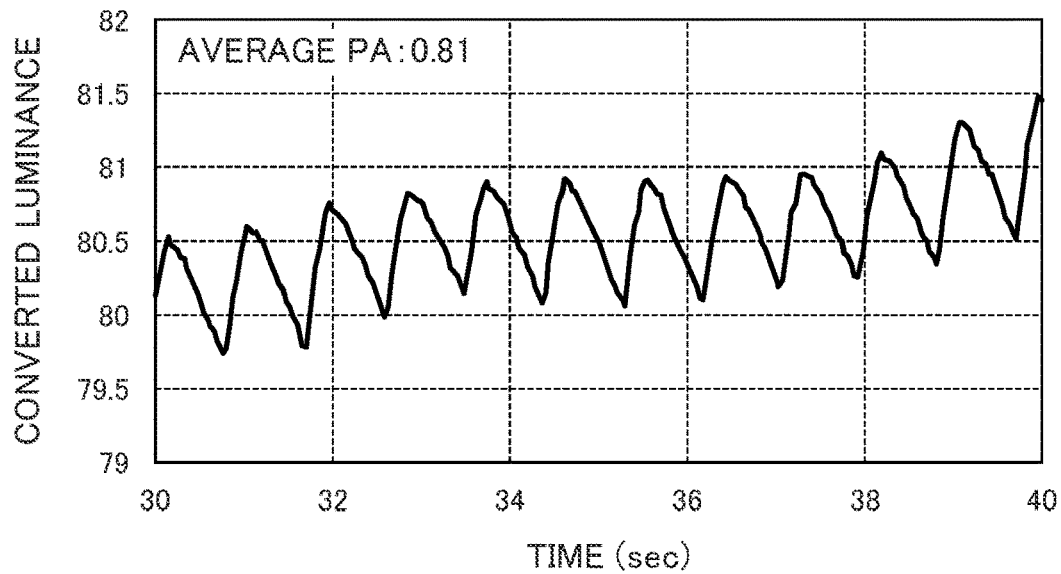
FIG. 17 is a graph showing an amplitude of the second portion after massage measured by an electronic device according to an embodiment of the present disclosure.

The change in the amplitude PA of the pulse wave before and after the event will be described with reference to FIGS. 14 to 17. FIG. 14 is a graph showing an amplitude of the first portion 61 before massage measured by the electronic device 1 according to the embodiment of the present disclosure, and is an enlarged view of a part of FIG. 9. FIG. 15 is a graph showing an amplitude of the second portion 62 before massage measured by the electronic device 1 according to the embodiment of the present disclosure, and is an enlarged view of a part of FIG. 10. FIG. 16 is a graph showing an amplitude of the first portion 61 after massage measured by the electronic device 1 according to the embodiment of the present disclosure, and is an enlarged view of a part of FIG. 11. FIG. 17 is a graph showing an amplitude of the second portion 62 after massage measured by the electronic device 1 according to the embodiment of the present disclosure, and is an enlarged view of a part of FIG. 12.

As can be seen from the comparisons among FIGS. 14 to 17, in the first portion 61, the average amplitude PA greatly increases from 0.57 (see FIG. 14) to 0.82 (see FIG. 16) before and after the massage. Also in the second portion 62, the average amplitude PA slightly increases from 0.70 (see FIG. 15) to 0.81 (see FIG. 17). In view of the above, it is found that, in the second portion 62, the increasing direction is reversed between the measurement result compared with the baseline and the measurement result compared with the amplitude PA. It is considered that this is because there was blood stagnated in the dark circle area under the eye due to poor blood circulation, which resulted in a high baseline state due to a large amount of average green light absorbed, but then the blood circulation was promoted by massage and the flow of stagnated blood was promoted, a result of which the amount of blood stagnated in that area decreased and the amount of green light absorbed decreased, whereby the baseline decreased. This idea can also be explained by reviewing the change in the amplitude PA. When the blood circulation state is poor, since the pulsation of the blood flowing through the blood vessel is weak, the value of the amplitude PA becomes small, and when the blood circulation is good, the pulsation of the blood becomes strong, and the value of the amplitude PA increases accordingly.

Here, the measurement results of the first portion 61 and the second portion 62 will be considered by focusing on the amplitude PA. In the comparison before and after the event of the first portion 61, although the average amplitude PA increased from 0.57 to 0.82 before and after the massage, the average amplitude PA of the second portion 62 also increased from 0.70 to 0.81 before and after the massage. On the other hand, when focusing on the baseline, the numerical value of the second portion 62 hardly changes before and after the event. It is considered that this is because the act of performing massage by himself/herself corresponds to the act of moving the entire body, and the blood flow of the whole body was promoted. In other words, it is considered that, since the capillaries in the cheek portion of the second portion 62 functioned normally, there was no stagnant blood in the portion, and only a change in pulsation was observed even in a state in which blood circulation was improved. From the viewpoint of accurately measuring the change in blood flow in the dark circle portion under the eye, it is preferable to eliminate the influence from the portion at which "the blood flow of the whole body was promoted" as much as possible.

Therefore, in the present embodiment, in order to acquire a measurement result in which an influence unrelated to an effect of an event is eliminated, the information processing unit 113 sets a blood flow increase index indicating the degree of increase in blood flow of the first portion 61 based on the measurement results of the first portion 61 and the second portion 62. The blood flow increase index i is calculated by the following Expression (1).

$$\text{blood flow increase index } i = \frac{\mu PA1\text{after}}{\mu PA2\text{after}} \bigg/ \frac{\mu PA1\text{before}}{\mu PA2\text{before}} \quad \text{Expression (1)}$$

μPA1before: average amplitude PA of the first portion 61 before the event

μPA2before: average amplitude PA of the second portion 62 before the event

μPA1after: average amplitude PA of first portion 61 after event

μPA2after: average amplitude PA of the second portion 62 after the event

The average amplitude refers to an average value of the amplitude of a predetermined time of interest (e.g., several tens of seconds).

The blood flow increase index i calculated by the expression (1) is an index value and has no units. In order to make it easier for the user to intuitively understand the change in the blood flow, the electronic device 1 of the present embodiment executes display processing of changing the display of the hue moving image 63 indicating the degree of increase in the blood flow in color by the numerical value of the blood flow increase index.

Figure 18:
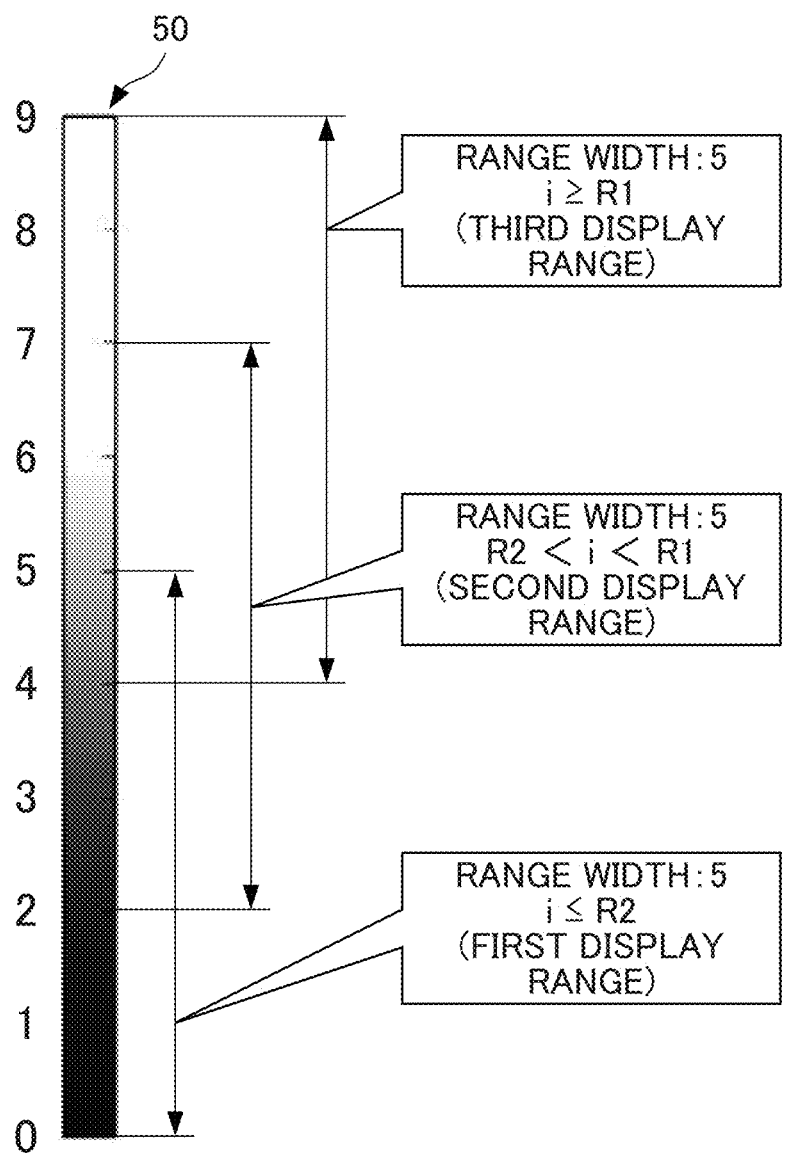
FIG. 18 is a schematic diagram showing the relationship between a blood flow increase index and a color map according to an embodiment of the present disclosure.

The processing for changing the display of the hue moving image 63 by the display processing unit 112 will be described with reference to FIG. 18. FIG. 18 is a schematic diagram showing the relationship between the blood flow increase index i and a color map 50 according to an embodiment of the present disclosure.

The display processing unit 112 includes a color map 50 serving as a reference for displaying a display image. The manner in which the color map 50 is displayed varies depending on a display range, which will be described later. As shown in FIG. 18, the color map 50 is hue information for determining a color corresponding to a luminance value. For the color map 50, for example, a jet color map 50 can be used.

In the following description, a scale of 0 to 9 is set in the color map 50 for convenience of description, and the range of hue is defined based on the scale. The scale 0 is the lowest coordinate of the color map 50, and the scale 9 is the highest coordinate of the color map 50. The low coordinate side is a hue of blue color (cold color), and the high coordinate side is a hue of reddish color (warm color). Furthermore, it is also assumed that the center coordinate of the color map 50 is in the middle of the scales 4 and 5.

In the present embodiment, a range width corresponding to the blood flow increase index is set from the three range widths of the first display range, the second display range, and the third display range. The first display range has a range width of scale 0 to 5 (range width of 5), the second display range has a range width of scale 2 to 7 (range width of 5), and the third display range has a range width of scale 4 to 9 (range width of 5). That is, the first display range is a range located on the low coordinate side, the second display range is a range located in the middle around the center coordinate, and the third display range is a range located on the high coordinate side. In this example, the lengths of the first display range, the second display range, and the third display range are the same; however, the set positions (coordinates) are shifted.

The display range is determined by comparing the blood flow increase index i with a reference value set for determining the display range. The reference value may be any numerical value so long as it allows the user to visually identify the difference when comparing the hue moving image 63 in a case where the reference value is not exceeded with the hue moving image 63 in a case where the reference value is exceeded, and is determined by experiment on the user, a theoretical value for calculating a visual recognition condition, or the like. When there are a plurality of display ranges to be selected, such as the first display range, the second display range, and the third display range, a plurality of reference values are also set in stages, such as the first reference value and the second reference value.

For example, in consideration of the range of the color map 50, a predetermined numerical value (hereinafter, R1) larger than 1 is set as the first reference value, and a numerical value (hereinafter, R2) smaller than R1 and larger than 1 is set as the second reference value. As described above, under the condition where the relationship of 1<R2<R1 is satisfied, the first display range is set when the blood flow increase index i calculated by the expression (1) satisfies the relationship of "i≤R2". The second display range is set when the blood flow increase index i satisfies the relationship "R2<i<R1", and the third display range is set when the blood flow increase index i satisfies the relationship "i≥R1".

Figure 19:
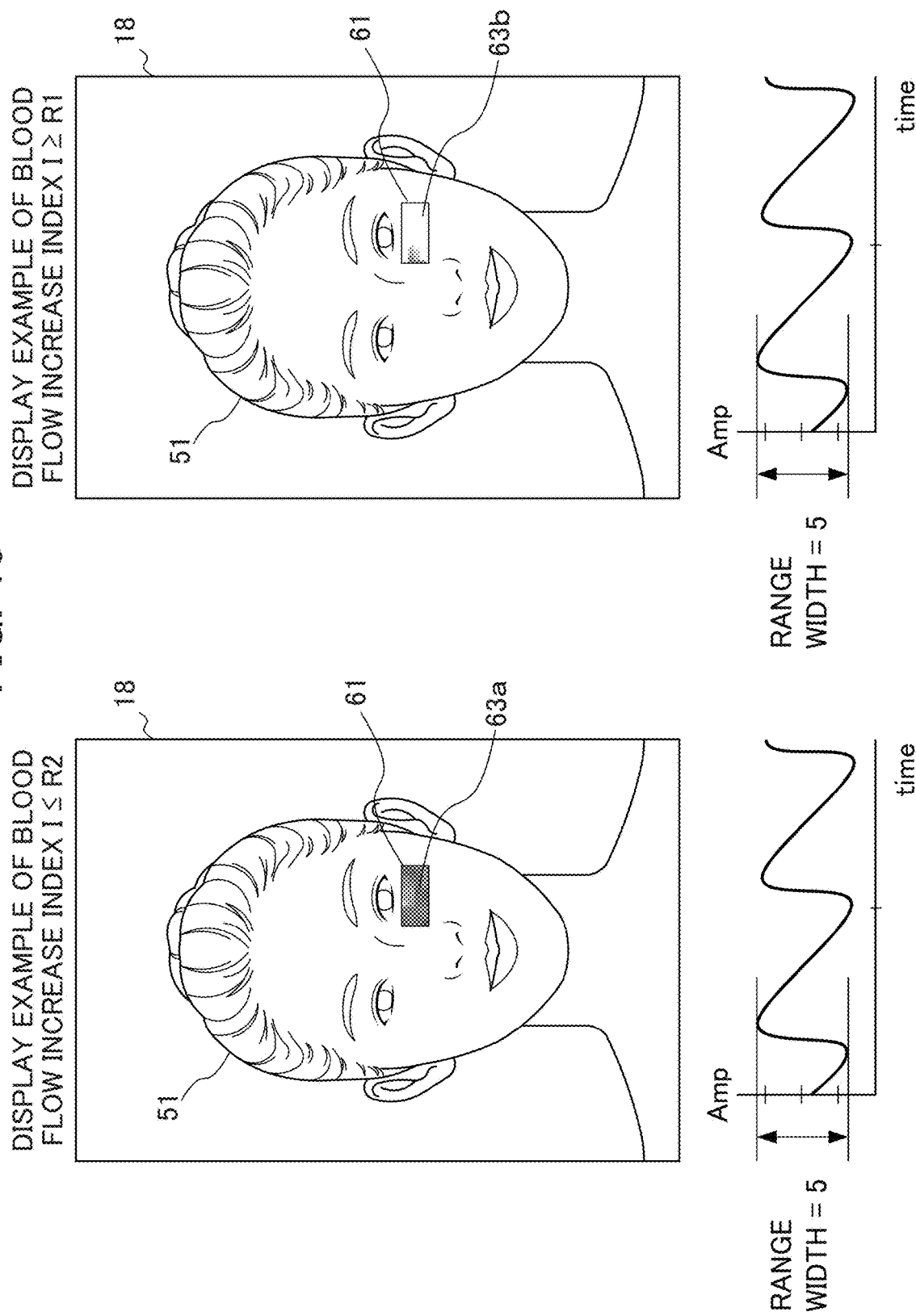
FIG. 19 is a diagram illustrating an example of a hue moving image generated in a display range determined based on a blood flow increase index according to an embodiment of the present disclosure.

FIG. 19 is a diagram showing an example of the hue moving image 63 generated in a display range determined based on a blood flow increase index according to an embodiment of the present disclosure. On the left side of FIG. 19, there is shown a hue moving image 63a showing the blood flow of the user before an event, in which the first display range located on the low coordinate side is set. On the other hand, on the right side of FIG. 19, there is shown a hue moving image 63b showing the blood flow of the user after the event, in which the third display range located on the high coordinate side is set. FIG. 19 also shows that a display capable of intuitively grasping the blood flow variation can be realized by changing the coordinates of the range width in accordance with the degree of the blood flow variation before and after the event.

Furthermore, the electronic device 1 of the present embodiment performs control in which the hue moving image 63 is displayed so that the maximum value of the amplitude PA of the pulse wave corresponds to the maximum value of the display range and the minimum value of the amplitude PA of the pulse wave corresponds to the minimum value of the display range. As a result, even when the display range changes, the color corresponding to the waveform of the pulse wave is appropriately set according to the determined display range, a result of which the movement of the blood flow that changes periodically can be appropriately visualized.

More specifically, the display processing unit 112 sets a color to be displayed in each area so that a positive peak of the amplitude corresponds to the maximum value of the range width and a negative peak of the amplitude corresponds to the minimum value of the range width in the pulse wave of the luminance of the small area. For example, in the first display range, scale 5 of the color map 50 corresponds to a positive peak of the pulse wave, and scale 0 thereof corresponds to a negative peak of the pulse wave. In the second display range, scale 7 of the color map 50 corresponds to the positive peak of the pulse wave and scale 2 thereof corresponds to the negative peak of the pulse wave. In the third display range, scale 9 of the color map 50 corresponds to the positive peak of the pulse wave, and scale 4 thereof corresponds to the negative peak of the pulse wave.

The display processing unit 112 sets a color to be displayed in a small area at a certain point in time based on the blood flow increase index i and the color map 50. It should be noted that, as described above, in the present embodiment, the hue moving image 63 displays, in a mosaic pattern, the change of the hue based on the temporal change in the luminance set for each small area. It should be noted that, when the hue moving image 63 before the event is generated, the display range is set with the increase rate set to 0. In this example, the first display range is a display range of the hue moving image 63 before a specific action.

Figure 20:
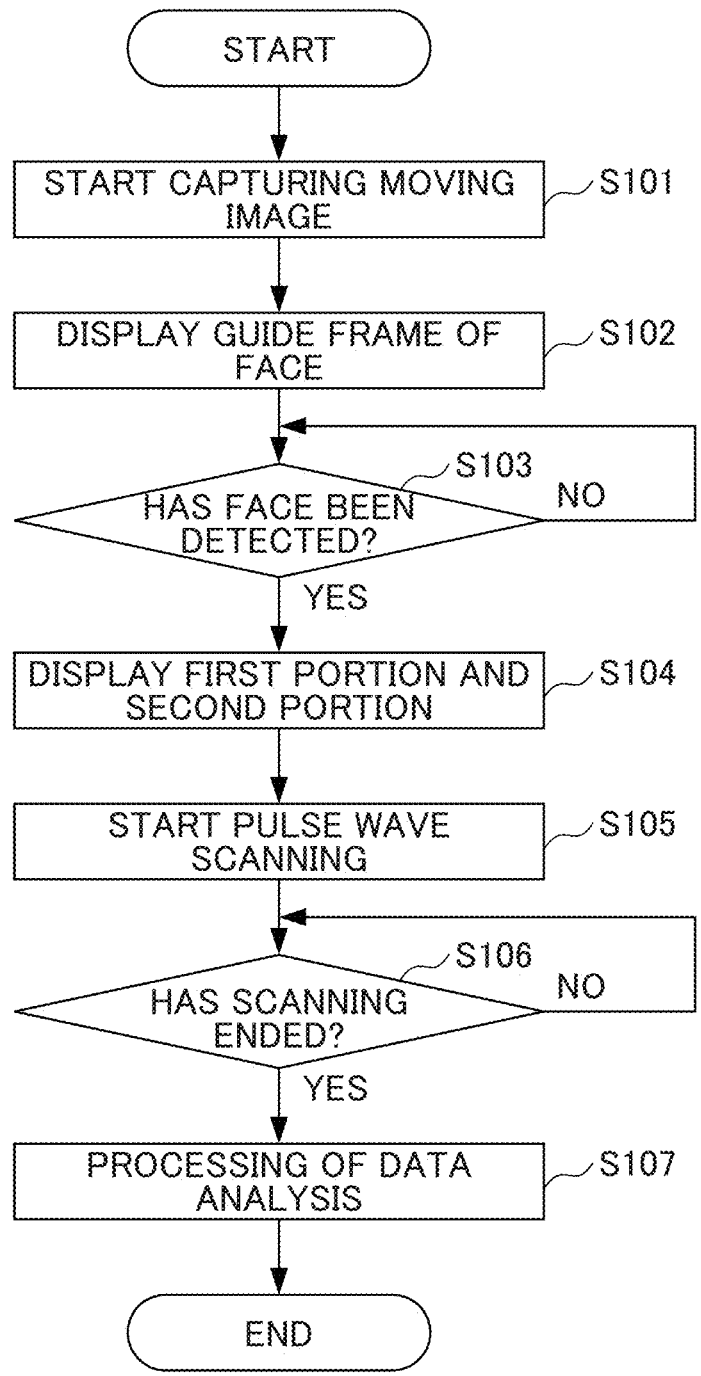
FIG. 20 is a flowchart illustrating a flow of measurement processing executed by an electronic device according to an embodiment of the present disclosure.

Next, the flow of processing for analyzing a video will be described with reference to FIG. 20. FIG. 20 is a flowchart showing a flow of measurement processing executed by the electronic device 1 of FIG. 1 having the functional configuration of FIG. 5.

As shown in FIG. 20, when the measurement processing is started, the video processing unit 111 starts capturing a video including a user as a subject by the imaging unit 16 (Step S101).

Next, the display processing unit 112 performs processing of displaying the guide frame 65 of the face as a guide image on the display unit 18 (Step S102). The guide frame 65 of the face is, for example, an ellipse indicated by a broken line in FIG. 6.

After the guide frame 65 for the face is displayed in Step S102, the video processing unit 111 determines whether or not the face of the user image 51 has entered the guide frame 65 of the face (Step S103). In Step S103, the video processing unit 111 identifies the position of the face of the user image 51 from the captured image by the facial recognition technique, and determines whether or not the position of the identified face is within the guide frame 65 of the face. The user adjusts the distance between the position of the face and the imaging unit 16 so that the face fits inside the guide frame 65 of the face of the imaging unit 16.

When the face of the user image 51 enters the guide frame 65 of the face, the processing proceeds to the processing of Step S104. When the face of the user image 51 does not enter the guide frame 65 of the face, the process returns to the processing of Step S102. That is, the guide frame 65 of the face and the text "move the face within the frame" are continuously displayed until the face of the user image 51 enters the guide frame 65 of the face.

When it is determined in Step S103 that the face of the user image 51 has entered the guiding frame 65 of the face, the video processing unit 111 identifies the first portion 61 and the second portion 62. Then, the first portion 61 and the second portion 62 identified by the display processing unit 112 are displayed on the display unit 18 (Step S104). In the present embodiment, the first portion 61 and the second portion 62 are displayed as a rectangular frame. The positions of the identified portions (the first portion 61 and the second portion 62) may be automatically set based on the positions of the respective feature points of the face (for example, the inner corners of the eyes, the outer corners of the eyes, the nose, the corners of the mouth, etc.) detected by the facial recognition technique, or may be adjusted by the user by operating the input unit 17 such as a touch screen.

After the first portion 61 and the second portion 62 are displayed in Step S104, the video processing unit 111 starts pulse wave scanning in Step S105. During the pulse wave scanning, a video including the user is captured by the imaging unit 16.

The video processing unit 111 continues the pulse wave scanning until a preset end condition is satisfied (Step S106). In a case in which the end condition is not satisfied, it is determined as No and the scanning continues, and in a case in which the end condition is satisfied, it is determined as Yes and the scanning ends. The end condition may be defined based on whether an imaging time has exceeded a preset imaging time, or based on whether the amount of information necessary for data analysis has been appropriately acquired.

Next, the video processing unit 111 analyzes the data acquired by the pulse wave scanning (Step S107). After the execution of the data analysis processing, the measurement processing ends. In the data analysis processing, as described above, processing of acquiring a change in luminance of the first portion 61 and the second portion 62 in the video is performed, for example.

Figure 21:
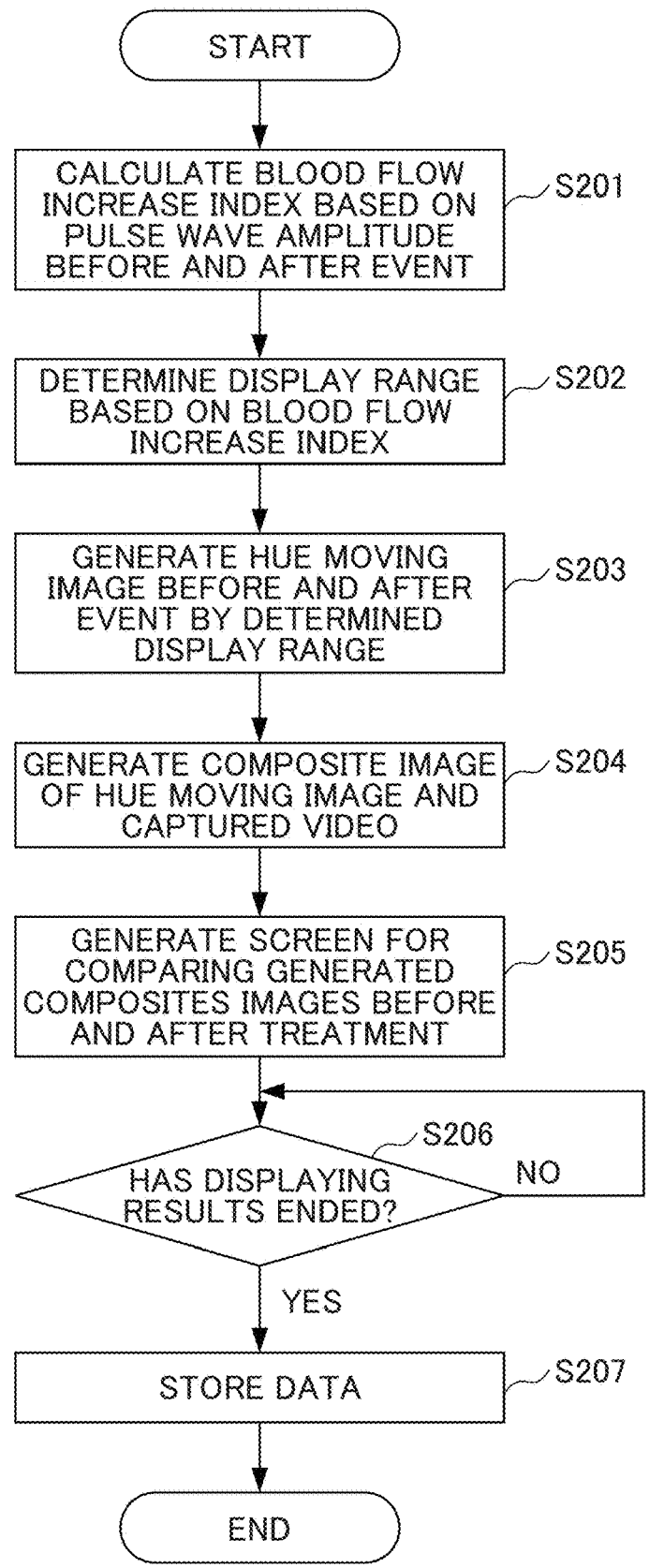
FIG. 21 is a flowchart illustrating a flow of display processing executed by an electronic device according to an embodiment of the present disclosure.

Next, the processing of displaying the measurement result acquired from the video before and after the event will be described with reference to FIG. 21. FIG. 21 is a flowchart showing a flow of display processing executed by the electronic device 1 of FIG. 1 having the functional configuration of FIG. 5.

As shown in FIG. 21, the information processing unit 113 calculates the blood flow increasing index i based on the pulse wave amplitudes PA before and after the event (Step S201). Here, the pulse wave amplitude PA before and after the event is the pulse wave amplitude PA of the first portion 61 and the second portion 62 before and after the event. In the present embodiment, the blood flow increase index i is calculated using Expression (1).

The display processing unit 112 determines a display range for displaying the hue moving images 63a and 63b based on the blood flow increase index i calculated in Step S201 (Step S202). The determination of the display range is determined by the hue moving image 63a indicating the state before the event and the hue moving image 63b indicating the state after the event.

The display processing unit 112 generates the hue moving image 63a of the first portion 61 before the event and the hue moving image 63b of the first portion 61 after the event based on the respective display ranges determined in Step S201 (Step S203). More specifically, the first hue moving image 63a indicating the state of the user before the event is generated based on the information indicating the temporal change in luminance of the green signal for each small region of the first portion 61 acquired from the video before the event. Similarly, the second hue moving image 63b indicating the state of the user after the event is generated based on the information indicating the temporal change in luminance of the green signal for each small region of the first portion 61 acquired from the video after the event.

The display processing unit 112 performs superimposition processing for compositing the hue moving images 63a and 63b with the user image 51 (video) (Step S204). For example, the display processing unit 112 detects a portion of the lower eye as the first portion 61 from the video captured by the imaging unit 16 by the face tracking processing. Then, the coordinates of the display unit coordinate system corresponding to the coordinates of the region of the detected portion in the imaging coordinate system are acquired based on the corresponding relationship of each coordinate system described above. Then, the display control unit 115 performs the superimposition processing of displaying the hue moving images 63a and 63b on the coordinates of the display unit coordinate system of the display unit 18.

Next, the display processing unit 112 generates a comparison image for simultaneously displaying the hue moving images 63a and 63b which are different along the time axis (Step S205). For example, a comparison image in which both the composite image before the display event and the composite image after the event are displayed is displayed on the display unit 18.

After the processing of Step S205, the display processing unit 112 waits for a display end instruction of a comparison screen from the user (Step S206). The display end instruction is notified by, for example, the operation of the input unit 17. When the display end instruction is notified, the display control unit 115 ends the display of comparison moving images, and the processing advances to Step S206.

The information processing unit 113 stores the data such as biological information acquired in the series of measurement processing in a measurement result storage unit 193 (Step S207). After the end of Step S207, the processing ends.

As described above, in the present embodiment, the video processing unit 111 acquires at least two types of luminance information with respect to the first portion 61. The two types of luminance information refer to the converted luminance of at least one pixel in the first portion 61 of a body of the video, and the average luminance of the entire region corresponding to the first portion 61 and the second portion 62 of the body of the first video. The average luminance is luminance information acquired to grasp the degree of increase of the blood flow, and the converted luminance is luminance information used to generate the hue moving image 63 in a mosaic pattern. On the other hand, since it is not necessary for the video processing unit 111 to generate the hue moving image 63 for the second portion 62, it is only necessary to acquire at least the average luminance.

The effects of the electronic device 1 of the present embodiment will be described.

The electronic device according to the present embodiment includes the video processing unit 111 and the information processing unit 113. The video processing unit 111 acquires, based on video information of a body in a first video obtained by imaging at least a part of the body, pulse wave information (pulse wave amplitude PA) indicating a pulse wave of a first portion 61 of the body and pulse wave information (pulse wave amplitude PA) indicating a pulse wave of a second portion 62 different from the first portion of the body. Furthermore, the video processing unit 111 acquires, based on video information of the body in a second video which is obtained by imaging a part of the body after imaging the first video (after an event), pulse wave information (pulse wave amplitude PA) indicating a pulse wave of the first portion 61 and pulse wave information (pulse wave amplitude PA) indicating a pulse wave of the second portion 62. The information processing unit 113 acquires, based on a relationship between the pulse wave information of the first portion and the pulse wave information of the second portion acquired from the first video, and a relationship between the pulse wave information of the first portion and the pulse wave information of the second portion acquired from the second video, a measurement result indicating a degree of change (increase) in blood flow from when imaging the first video to when imaging the second video.

With such a configuration, it is possible to eliminate the change in the pulse wave information caused by the change in the situation that occurs from the time of capturing the first video until capturing the second video. For example, the condition may be changed between the time of first video capturing and the time of second video capturing, such as a change in the color of the user's skin due to the luminance of illumination, psychological factors of the user, physical condition, tanning, and the like. If the effect of the event is measured only with respect to the first portion 61 in a case in which such a change occurs, it is impossible to determine whether the event causes the blood flow variation of the first portion 61, whether the change in the condition causes the blood flow variation of the first portion 61, or whether both effects occur. In this respect, according to the configuration of the present embodiment, since the change of the second portion 62 at a position different from the first portion 61 is considered, the degree of the change in the blood flow occurring only in the first portion 61 can be accurately acquired.

Furthermore, the pulse wave information acquired by the video processing unit 111 according to the present embodiment is an average amplitude within a predetermined time.

With such a configuration, it is possible to eliminate the influence of the change in the blood flow caused by the user's own behavior, which cannot be acquired by the overall average value of the pulse wave, and to more accurately grasp the degree of the change in the blood flow generated in the first portion 61.

The information processing unit 113 is further configured to perform operation including calculating a blood flow increase index i as a measurement result, based on a ratio of an average amplitude PA of the first portion 61 to an average amplitude PA of the second portion 62 acquired from the first video, and a ratio of an average amplitude PA of the first portion 61 to an average amplitude PA of the second portion 62 acquired from the second video.

With such a configuration, the degree of increase in the blood flow can be quantitatively expressed by numerical values.

Furthermore, the electronic device 1 according to the present embodiment further includes the display processing unit 112 that generates a display video corresponding to a blood flow variation at a part of the body, and the display processing unit 112 determines a display method for the hue moving image 63 as a display image based on the measurement result acquired by the information processing unit 113.

With such a configuration, the user can intuitively grasp changes in the blood flow which are different along the time axis.

Furthermore, the display processing unit 112 according to the present embodiment is further configured to perform operation including determining the display method for the display video by setting, as a display range, a range on a high coordinate side in a range of the color map 50 for a hue of display colors as a degree of increase in a blood flow is greater, and setting, as the display range, a range on a low coordinate side in the range of the color map 50 for a hue of display colors as the degree of increase in the blood flow is smaller.

With such a configuration, it is possible to inform the user of changes in the blood flow in two videos which are different along a time axis in an easy-to-understand manner. For example, even if the blood flow is improved as a result of a specific action, since the waveform of the pulse wave is displayed as the color map 50 according to the display in an embodiment of the present disclosure, it is difficult to distinguish the difference before and after the specific action even if the pulse wave is simply displayed in the hue moving image 63 in the same display range. In this respect, according to the configuration of the present embodiment, the hue moving image 63 can be generated which reflects the degree of change in the blood flow after the event, a result of which the measurement result can be visually displayed in an easy-to-understand manner due to the difference in the tendency of the displayed colors.

[Modifications]

The present disclosure is not limited to the above-described embodiments, and modifications, improvements, and the like within the scope that can achieves the object of the present disclosure are included in the present disclosure. For example, the embodiments described above may be modified as the following modifications.

In the above embodiment, the second portion 62 is provided at a single location; however, the present disclosure is not limited to this type. A plurality of second portions 62 may be set. It is preferable for the second portion 62 to be appropriately set empirically or theoretically at a position where the second portion 62 appropriately functions as a reference point based on the position of the first portion 61.

In the above embodiment, the hue moving image 63 in which a change in hue is displayed in a mosaic pattern is described as an example; however, the display format is not limited to this format. For example, instead of processing of displaying in a mosaic pattern, the hue moving image 63 may be displayed at a single location in a specific portion (for example, a portion of a cheek). In this case, the color to be displayed at a certain point in time may be determined based on the pulse wave information used to determine the display range.

In the above embodiment, the real image is composited in the video; however, the display format is not limited to this format. A hue moving image matching the avatar image may be created, and blood flow variation may be displayed by animation using bluish or reddish colors, for example.

In the above embodiment, a configuration has been described in which the comparison processing using the converted luminance value subjected to processing of converting with respect to the detected luminance; however, the present disclosure is not limited to this configuration. The converted luminance value is one mode indicating the level of luminance, and thus, the conversion processing may be omitted from the above embodiment, and the comparison processing may be performed using the detected luminance value without performing the conversion processing.

In the above embodiment, an example has been described in which the display processing unit 112 changes the position of the range width in the color map 50 based on the blood flow increase index I; however, the present disclosure is not limited to this configuration. The display processing unit 112 may set the range width of the display range around the color corresponding to the center coordinate of the display range to be wider than the range width of the display range which is applied when the increase rate of the second amplitude with respect to the first amplitude is relatively low as the blood flow increase index is larger, and the display processing unit 112 may set the range width of the display range around the color corresponding to the center coordinate of the display range to be narrower than the range width of the display range which is applied when the increase rate of the second amplitude with respect to the first amplitude is relatively high as the increase rate of the second amplitude with respect to the first amplitude is smaller. With such a configuration, the color changes within a narrow range when the degree of change is small in the hue moving image 63; whereas, the color changes dramatically when the degree of change is large therein, a result of which the degree of the blood flow variation occurring between the first video and the second video can be reflected in the display of the hue moving image 63 in an easy-to-understand manner. Alternatively, the display processing unit 112 may determine the brightness of the display of the display video based on the blood flow increase index i. For example, when the degree of change is small in the hue moving image 63, the color is changed at a low luminance; whereas, when the degree of change is large, the color which is bright is changed at a high luminance, a result of which the degree of the blood flow variation occurring between the first video and the second video can be reflected in an easy-to-understand manner in the display of the hue moving image 63. As described above, the display method of the display image can be appropriately changed.

It is possible to incorporate a mirror unit having a reflecting surface into the display unit 18 of the electronic device 1 of the above embodiment. In this case, the mirror unit is realized by a half mirror having both transmission characteristics and reflection characteristics, as an optical characteristic. The mirror unit is disposed to be superimposed on the front surface of the display unit 18 in a direction in which the user visually recognizes the mirror unit. With such an configuration, for example, the user can visually recognize not the user image captured by the image unit 16, but rather the face of the user, which is reflected by the mirror unit, and various kinds of information (for example, a composite image) displayed on the display unit 18 and transmitted through the mirror unit at the same time. That is, in the above-described embodiment above, the user image captured by the imaging unit 16 as a subject is visually recognized as a real image of the user; however, in the present modification example, a mirror image of the user reflected by the mirror unit is visually recognized as the real image of the user. Even in this way, it is possible to provide the same effect as in the above-described embodiment.

In the above embodiment, the smart mirror is described as an example of the electronic device of the present disclosure; however, present disclosure is not limited thereto. For example, the electronic device may include an imaging unit, a cover dedicated to isolating the imaging unit from the outside, and an illumination unit disposed in the cover. According to this electronic device, it is possible to acquire a video in a state in which the influence of disturbance is suppressed and the brightness in the cover is kept constant.

Other Modified Examples

For example, in the above embodiment, it is assumed that the electronic device 1 cooperates with the respective servers included in the server group 3, but the functions of the respective servers may be added to the electronic device 1, and all the processes may be performed only in the electronic device 1.

In addition, in the above embodiment, the electronic device 1 to which the present invention is applied has been described by way of example of an electronic device incorporated in a portable self-standing mirror, but the present invention is not particularly limited thereto. For example, the present invention can be applied to an electronic device incorporated into a large mirror such as a full-length mirror, an electronic device incorporated into a stationary bathroom vanity, and a mirror-shaped electronic device installed in a bathroom.

The processing sequence described above can be executed by hardware, and can also be executed by software. In other words, the functional configuration of FIG. 5 is merely an illustrative example, and the present invention is not particularly limited thereto. More specifically, the types of functional blocks employed to realize the above-described functions are not particularly limited to the examples shown in FIG. 5, so long as the electronic device 1 can be provided with the functions enabling the aforementioned processing sequence to be executed in its entirety.

In addition, a single functional block may be configured by a single piece of hardware, a single installation of software, or a combination thereof. The functional configurations of the present embodiment are realized by a processor executing arithmetic processing, and processors that can be used for the present embodiment include a unit configured by a single unit of a variety of single processing devices such as a single processor, multi-processor, multi-core processor, etc., and a unit in which the variety of processing devices are combined with a processing circuit such as ASIC (Application Specific Integrated Circuit) or FPGA (Field-Programmable Gate Array).

In the case of having the series of processing executed by software, the program constituting this software is installed from a network or recording medium to a computer or the like. The computer may be a computer equipped with dedicated hardware. In addition, the computer may be a computer capable of executing various functions, e.g., a general purpose personal computer, by installing various programs.

The storage medium containing such a program can not only be constituted by the removable medium 100 of FIG. 4 distributed separately from the device main body for supplying the program to a user, but also can be constituted by a storage medium or the like supplied to the user in a state incorporated in the device main body in advance. The removable medium 100 is composed of, for example, a magnetic disk (including a floppy disk), an optical disk, a magnetic optical disk, or the like. The optical disk is composed of, for example, a CD-ROM (Compact Disk-Read Only Memory), a DVD (Digital Versatile Disk), Blu-ray (Registered Trademark) or the like. The magnetic optical disk is composed of an MD (Mini-Disk) or the like. The storage medium supplied to the user in a state incorporated in the device main body in advance is constituted by, for example, the ROM 12 of FIG. 4 in which the program is recorded or a hard disk included in the storage unit 19 of FIG. 4 or 5, etc.

It should be noted that, in the present specification, the steps defining the program recorded in the storage medium include not only the processing executed in a time series following this order, but also processing executed in parallel or individually, which is not necessarily executed in a time series. Further, in the present specification, the terminology of the system means an entire apparatus including a plurality of apparatuses and a plurality of units.

The embodiments of the present invention described above are only illustrative, and are not to limit the technical scope of the present invention. The present invention can assume various other embodiments. Additionally, it is possible to make various modifications thereto such as omissions or replacements within a scope not departing from the spirit of the present invention. These embodiments or modifications thereof are within the scope and the spirit of the invention described in the present specification, and within the scope of the invention recited in the claims and equivalents thereof.

What is claimed is:

1. An electronic device comprising:
   a memory; and
   at least one processor,
   wherein the at least one processor executes a program stored in the memory to perform operations comprising:
      acquiring, based on video information of a body in a first video obtained by imaging at least a part of the body, pulse wave information indicating a pulse wave of a first portion of the body and pulse wave information indicating a pulse wave of a second portion different from the first portion of the body;
      acquiring, based on video information of the body in a second video is obtained by imaging at least the part of the body after imaging the first video, pulse wave information indicating a pulse wave of the first portion and pulse wave information indicating a pulse wave of the second portion; and
      acquiring a measurement result indicating a degree of change in a blood flow from when the first video was imaged to when the second video was imaged, based on (i) a relationship between the pulse wave information of the first portion and the pulse wave information of the second portion acquired from the first video, and (ii) a relationship between the pulse wave information of the first portion and the pulse wave information of the second portion acquired from the second video.

2. The electronic device according to claim 1, wherein the pulse wave information comprises information on an average amplitude of the pulse wave within a predetermined period of time.

3. The electronic device according to claim 2, wherein the at least one processor is further configured to perform an operation comprising calculating, as the measurement result, a blood flow increase index based on (i) a ratio of the average amplitude of the pulse wave of the first portion to the average amplitude of the pulse wave of the second portion acquired from the first video, and (ii) a ratio of the average amplitude of the pulse wave of the first portion to the average amplitude of the pulse wave of the second portion acquired from the second video.

4. The electronic device according to claim 1, wherein the at least one processor is further configured to perform operations comprising:
   generating a display video corresponding to a blood flow variation at the part of the body; and
   determining a display method for the display video based on the measurement result.

5. The electronic device according to claim 4, wherein the determining the display method for the display video comprises:
   setting, as a display range, a range on a higher coordinate side in a color map range for a hue of display colors as a degree of increase in the blood flow is greater; and
   setting, as the display range, a range on a lower coordinate side in the color map range as the degree of increase in the blood flow is smaller.

6. A non-transitory computer-readable storage medium storing a program that is executed by a computer that comprises at least one processor to control an electronic device, the program being executable to cause the computer to perform operations comprising:
   acquiring, based on video information of a body in a first video obtained by imaging at least a part of the body, pulse wave information indicating a pulse wave of a first portion of the body and pulse wave information indicating a pulse wave of a second portion different from the first portion of the body;
   acquiring, based on video information of the body in a second video obtained by imaging at least the part of the body after imaging the first video, pulse wave information indicating a pulse wave of the first portion and pulse wave information indicating a pulse wave of the second portion; and
   acquiring a measurement result indicating a degree of change in blood flow from when imaging the first video to when imaging the second video, based on (i) a relationship between the pulse wave information of the first portion and the pulse wave information of the second portion acquired from the first video, and (ii) a relationship between the pulse wave information of the first portion and the pulse wave information of the second portion acquired from the second video.

7. A control method for an electronic device executed by a computer including at least one processor, the control method causing the at least one processor to execute a program stored in a memory to perform operations comprising:

acquiring, based on video information of a body in a first video obtained by imaging at least a part of the body, pulse wave information indicating a pulse wave of a first portion of the body and pulse wave information indicating a pulse wave of a second portion different from the first portion of the body;

acquiring, based on video information of the body in a second video is obtained by imaging at least the part of the body after imaging the first video, pulse wave information indicating a pulse wave of the first portion and pulse wave information indicating a pulse wave of the second portion; and acquiring a measurement result indicating a degree of change in a blood flow from when the first video was imaged to when the second video was imaged, based on (i) a relationship between the pulse wave information of the first portion and the pulse wave information of the second portion acquired from the first video, and (ii) a relationship between the pulse wave information of the first portion and the pulse wave information of the second portion acquired from the second video.

* * * * *

UNITED STATES PATENT AND TRADEMARK OFFICE
CERTIFICATE OF CORRECTION

PATENT NO. : 11,800,989 B2
APPLICATION NO. : 17/172241
DATED : October 31, 2023
INVENTOR(S) : Takahiro Tomida and Toshihiko Otsuka It is certified that error appears in the above-identified patent and that said Letters Patent is hereby corrected as shown below:

In the Claims

Column 21, Line 60, Claim 1, after "video" delete "is".

Column 23, Line 11, Claim 7, after "video" delete "is".

Signed and Sealed this
Twenty-third Day of January, 2024

Katherine Kelly Vidal
*Director of the United States Patent and Trademark Office*